United States Patent [19]
Connell et al.

[11] Patent Number: 5,606,014
[45] Date of Patent: Feb. 25, 1997

[54] IMIDE OLIGOMERS AND CO-OLIGOMERS CONTAINING PENDENT PHENYLETHYNYL GROUPS AND POLYMERS THEREFROM

[75] Inventors: John W. Connell, Yorktown; Joseph G. Smith, Jr., Grafton; Paul M. Hergenrother, Yorktown, all of Va.

[73] Assignee: The United States of America as represented by the United States National Aeronautics and Space Administration, Washington, D.C.

[21] Appl. No.: 511,422

[22] Filed: Aug. 4, 1995

[51] Int. Cl.$^6$ .......................... C08G 73/10; C08G 69/26
[52] U.S. Cl. .......................... 528/353; 528/125; 528/128; 528/170; 528/171; 528/172; 528/173; 528/174; 528/175; 528/176; 528/183; 528/185; 528/188; 528/220; 528/229; 528/350; 524/600; 524/607; 526/262; 526/285; 526/935; 428/411.1; 428/473.5
[58] Field of Search .......................... 528/125, 128, 528/353, 171, 174, 350, 175, 220, 229, 176, 170, 172, 173, 183, 188, 185; 524/600, 607; 526/262, 285, 935; 428/411.1, 473.5

[56] References Cited

U.S. PATENT DOCUMENTS

| | | | |
|---|---|---|---|
| 4,837,300 | 6/1989 | St. Clair et al. | 528/353 |
| 5,138,028 | 8/1992 | Paul et al. | 528/353 |

OTHER PUBLICATIONS

*Polymer Preprints*, vol. 30, No. 1 (Apr. 1989), "Model Branched Poly(methylmethacrylates of Controlled Molecular Weight and Architecture; Synthesis Characterization", Siochi et al, pp. 141–143, 137–140.

*Primary Examiner*—Jeffrey C. Mullis
*Assistant Examiner*—P. Hampton-Hightower
*Attorney, Agent, or Firm*—George F. Helfrich

[57] ABSTRACT

Controlled molecular weight imide oligomers and co-oligomers containing pendent phenylethynyl groups (PEPIs) and endcapped with nonreactive or phenylethynyl groups have been prepared by the cyclodehydration of the precursor amide acid oligomers or co-oligomers containing pendent phenylethynyl groups and endcapped with nonreactive or phenylethynyl groups. The amine terminated amide acid oligomers or co-oligomers are prepared from the reaction of dianhydride(s) with an excess of diamine(s) and diamine containing pendent phenylethynyl groups and subsequently endcapped with a phenylethynyl phthalic anhydride or monofunctional anhydride. The anhydride terminated amide acid oligomers and co-oligomers are prepared from the reaction of diamine(s) and diamine containing pendent phenylethynyl group(s) with an excess of dianhydride(s) and subsequently endcapped with a phenylethynyl amine or monofunctional amine. The polymerizations are carried out in polar aprotic solvents such as under nitrogen at room temperature. The amide acid oligomers or co-oligomers are subsequently cyclodehydrated to the corresponding imide oligomers. The polymers and copolymers prepared from these materials exhibit a unique and unexpected combination of properties.

44 Claims, 6 Drawing Sheets

IMIDE OLIGOMERS AND CO-OLIGOMERS CONTAINING PENDENT PHENYLETHYNYL GROUPS AND POLYMERS THEREFROM

ORIGIN OF THE INVENTION

This invention described herein was made by employees of the United States Government and may be manufactured and used by or for the Government or government purposes without payment of any royalties therein or thereof.

BACKGROUND OF THE INVENTION

Polyimides (PI) are heterocyclic polymers commonly prepared by the condensation reaction of an aromatic diamine with an aromatic dianhydride or derivative thereof and having a repeat unit of the general structure

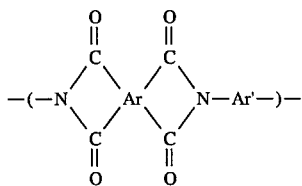

where Ar is a tetravalent aromatic radical such as 1,2,4,5-tetrasubstituted benzene. Ar may also be a bis(o-diphenylene) having the general structure

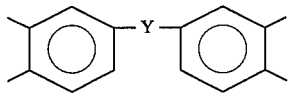

where Y=nil, O, S, $SO_2$, CO, $C(CH_3)_2$, or any other appropriate divalent radical. Ar' is a divalent aromatic radical which may be 1,3-phenylene, 1,4-phenylene, 4,4'-biphenylene, 4,4'-oxydiphenylene, 4,4'-sulfonyldiphenylene, or any other appropriate divalent radical.

The synthesis and characterization of PI has been extensively studied and documented. Reviews on PI are available. [J. W. Verbicky, Jr., "Polyimides" in Encyclopedia of Polymer Science and Engineering, $2^{nd}$ Ed., John Wiley and Sons, New York, Vol. 12, 364 (1988); C. E. Sroog, Prog. Polym. Sci., 16, 591 (1991)].

A variety of monomers, oligomers and polymers containing ethynyl (acetylenic) and substituted ethynyl (i.e. phenylethynyl) groups have been reported. The ethynyl groups in the polymer is either pendent to the chain, in the chain, or at the chain ends. Many of these materials have been used to prepare coatings, moldings, adhesives and composites [P. M. Hergenrother, "Acetylene Terminated Prepolymers" in Encyclopedia of Polymer Science and Engineering, John Wiley and Sons, New York, Vol. 1, 61 (1985)]. Good processability by either solution casting and/or compression molding have been observed for the ethynyl and substituted ethynyl containing materials. In general, thermally cured ethynyl and substituted ethynyl containing materials exhibit a favorable combination of physical and mechanical properties. Some ethynyl endcapped materials such as the Thermid® resins are commercially available (National Starch and Chemical Co., Bridgewater, N.J. 08807). Phenylethynyl containing amines have been used to terminate imide oligomers [F. W. Harris, A. Pamidimuhkala, R. Gupta, S. Das, T. Wu, and G. Mock, Poly. Prep., 24 (2), 325, 1983; F. W. Harris, A. Pamidimuhkala, R. Gupta, S. Das, T. Wu, and G. Mock, J. Macromol. Sci.-Chem., A21 (8 & 9), 1117 (1984); C. W. Paul, R. A. Schultz, and S. P. Fenelli, "High-Temperature Curing Endcaps For Polyimide Oligomers" in Advances in Polyimide Science and Technology, (Ed. C. Feger, M. M. Khoyasteh, and M. S. Htoo), Technomic Publishing Co., Inc., Lancaster, Pa., 1993, p. 220; R. G. Byrant, B. J. Jensen, and P.M. Hergenrother, Poly. Prepr., 34 (1), 566, 1993]. Imide oligomers terminated with ethynyl phthalic anhydride [P. M. Hergenrother, Poly. Prep., 21 (1), 81, 1980], substituted ethynyl phthalic acid derivatives [S. Hino, S. Sato, K. Kora, and O. Suzuki, Jpn. Kokai Tokkyo Koho JP 63, 196, 564. Aug. 15, 1988; Chem. Abstr., 115573w, 110, ( 1989)] and phenylethynyl containing phthalic anhydrides have been reported. Imide oligomers containing pendent substituted ethynyl groups [F. W. Harris, S. M. Padaki, and S. Varaprath, Poly. Prepr., 21 (1), 3, 1980 (abstract only), B. J. Jensen, P. M. Hergenrother, and G. Nwokogu, Polymer, 34 (3), 630, 1993; B. J. Jensen and P. M. Hergenrother, U.S. Pat. No. 5,344,982 (Sep. 6, 1994)] have been reported.

This present invention constitutes new composition of matter. It concerns novel diamines containing phenylethynyl groups and new imide oligomers and co-oliogmers containing pendent phenylethynyl groups. The polymers and copolymers prepared from these materials exhibit a unique and unexpected combination of properties that includes higher glass transition temperatures after curing and higher retention of neat resin, adhesive and carbon fiber reinforced mechanical properties at temperatures up to 204° C. under wet conditions without sacrificing melt flow behavior and processability as compared to similar materials.

Another object of the present invention is to provide materials that are useful as adhesives, coatings, films, moldings and composite matrices.

Another object of the present invention is the composition of several new diamines containing pendent phenylethynyl groups.

SUMMARY OF THE INVENTION

According to the present invention the foregoing and additional objects were obtained by synthesizing controlled molecular weight imide oligomers and co-oligomers containing pendent phenylethynyl groups and endcapped with phenylethynyl groups or nonreactive groups by different methods. Amide acid oligomers and co-oligomers containing pendent phenylethynyl groups (PEPAAs) were prepared by the reaction of dianhydride(s) with an excess of diamine(s) and diamine containing pendent phenylethynyl group(s) and endcapped with 4-phenylethynylphthalic anhydride or phthalic anhydride under a nitrogen atmosphere at room temperature in N-methyl-2-pyrrolidinone (NMP). Additionally, PEPAAs were prepared by the reaction of diamine(s) and diamine containing pendent phenylethynyl group(s) with an excess of dianhydride(s) and endcapped with a 3-aminophenoxy-4'phenylethynylbenzophenone under a nitrogen atmosphere at room temperature in NMP. The imide oligomers and co-oligomers containing pendent phenylethynyl groups (PEPI) were prepared by cyclodehydration of the precursor PEPAA oligomers in NMP by azeotropic distillation with toluene. The direct preparation of PEPIs has been performed in m-cresol containing isoquinoline at elevated temperature. Amide acid oligomers and co-oligomers containing pendent phenylethynyl groups can be prepared by the reaction of diamine(s) and diamine containing pendent phenylethynyl group(s) with an excess of dianhydride(s) and endcapped with a monofunctional amine under a nitrogen atmosphere at room temperature in NMP. Imide oligomers and co-oligomers containing pendent phenylethynyl groups can be prepared by the reaction of the half alkyl ester of aromatic tetracarboxylic acids with aromatic diamines and diamine containing pendent phenylethynyl group(s) and endcapped with the half alkyl ester of phenylethynyl substituted phthalic acid, the half alkyl ester of phthalic acid, phenylethynyl amine, or monofunctional amine by heating in NMP. PEPIs prepared by the alkyl ester route can also be prepared by heating neat or in solvents such as m-cresol. Imide oligomers and co-oligomers containing pendent phenylethynyl groups can be prepared by the polymerization of monomeric reactants (PMR) approach by heating a mixture of a diamine and diamine containing pendent phenylethynyl group(s) and the ethyl ester derivatives of dianhydride(s) and endcapped with phenylethynylphthalic anhydride, monofunctional anhydride, phenylethynyl amine, or monofunctional amine.

In addition, the amine terminated PEPAA oligomer or co-oligomer or the anhydride terminated PEPAA oligomer or co-oligomer can be cyclodehydrated to the corresponding amine terminated PEPI or the anhydride terminated PEPI oligomer or co-oligomer, respectively, and the appropriate endcapper subsequently reacted with the soluble amine terminated PEPI oligomer or co-oligomer or the soluble anhydride terminated PEPI oligomer or co-oligomer, respectively. The PEPI oligomer or co-oligomer must be soluble in order to perform this endcapping reaction. Upon reaction of the amine terminated PEPI oligomer or co-oligomer or the anhydride terminated PEPI oligomer or co-oligomer with the endcapper, the temperature is increased to effect cyclodehydration to complete imidization. The inherent viscosities ($\eta_{inh}$) of the PEPAA oligomers and co-oligomers ranged from 0.21 to 0.65 dL/g and the $\eta_{inh}$ of high molecular weight unendcapped PEPAA was 0.85 dL/g. The glass transition temperatures ($T_g$) of the uncured as-isolated PEPIs ranged from 209°–269° C. In some cases, a crystalline melt temperature was observed for the uncured PEPIs. The temperature of onset and peak exotherm due to reaction of the phenylethynyl group was ~350° C. and ~411° C., respectively. After curing at 350° C. for 1 h in a sealed DSC pan the $T_g$ of the cured polymers ranged from 255°–313° C. Thermogravimetric analysis (TGA) at a heating rate of 2.5° C./min of the uncured as-isolated PEPI powders showed no weight loss occurring below 300° C. in air or nitrogen with a 5% weight loss occurring ~475° C. in air and ~517° C. in nitrogen. After a thermal cure (350° C./mold/1 h), TGA at a heating rate of 2.5° C./min of the cured polymers showed no weight loss occurring below 300° C. in air or nitrogen with a 5% weight loss occurring ~495° C. in air and ~510° C. in nitrogen. The tensile strength, tensile modulus, and break elongation for unoriented thin films ranged from 18.9–21.8 ksi, 457–600 ksi, and 4–20% at 23° C.; and 10.1–14.0 ksi, 290–411 ksi, and 5–34% at 177° C.; and 9.2–12.2 ksi, 267–372 ksi, and 6–30% at 200° C., respectively. The polymers prepared from these materials exhibit higher glass transition temperatures with no apparent reduction in melt flow behavior as compared to similar materials. The $G_{IC}$ (critical strain energy release rate) of compression molded samples of PEPIs ranged from 2.9 in lb/in$^2$ to 10.3 in lb/in$^2$. The titanium (Ti) to Ti tensile shear properties performed on PASA Jell 107 surface treated adherends were 3900 at 23° C. and 4100 at 177° C. The Ti to Ti tensile shear properties performed on chromic acid anodized (5 V) surface treated adherends were 4300 at 23° C. and 4100 at 177° C. The flexural properties of composite panels with a unidirectional lay-up gave flexural strength and flexural modulus which ranged from 233.5–260.3 ksi and 21.08–21.52 Msi at 23° C. and 190.3–219.4 ksi and 18.73–20.58 Msi at 177° C., respectively. In general, composite specimens exhibited higher mechanical properties when tested at room temperature and better retention of those properties when tested at 177° C. than similar materials.

The diamines containing pendent phenylethynyl group(s) were prepared by the palladium catalyzed reaction of phenylacetylene with bromo substituted dinitro compounds and subsequently reduced to the corresponding diamines containing pendent phenylethynyl group(s) as shown in FIG. 1. The catenation of the phenylethynyl group on the phenyl ring may be para or meta and multiple phenyl rings may have mixed connecting positions. In general, this synthethic route to diamines containing pendent phenylethynyl groups is more cost effective than other routes. The general reaction sequence for the synthesis of both uncontrolled and controlled molecular weight polymers and copolymers is represented in FIGS. 2, 3,4,5 and 6.

The polymers and copolymers prepared from these materials exhibit a unique and unexpected combination of properties that includes higher glass transition temperatures after curing, higher tensile moduli and higher retention of neat resin, adhesive and carbon fiber reinforced mechanical properties at temperatures up to 204° C. when wet without sacrificing melt flow behavior and processability as compared to similar materials.

DESCRIPTION OF THE PREFERRED EMBODIMENTS

Figure 1:
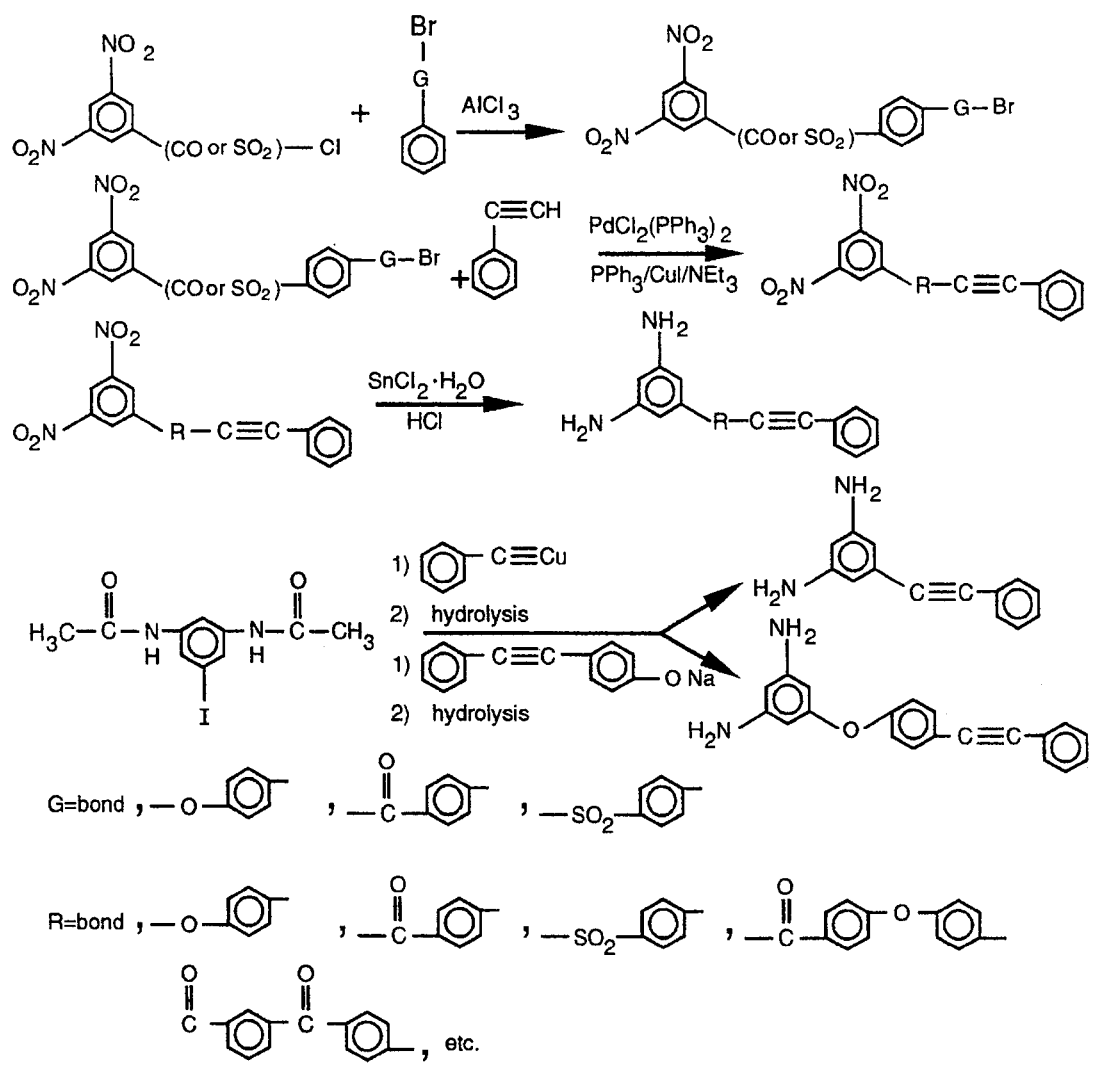
FIG. 1 is a schematic of the synthesis of diamines containing pendent phenylethynyl groups according to the present invention.

Novel diamines containing pendent phenylethynyl groups were prepared according to FIG. 1 having the following chemical structure:

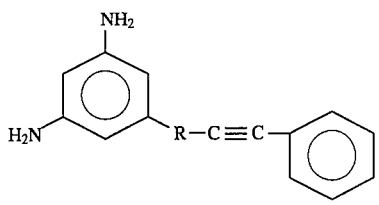

wherein R is a radical selected from the group consisting of:

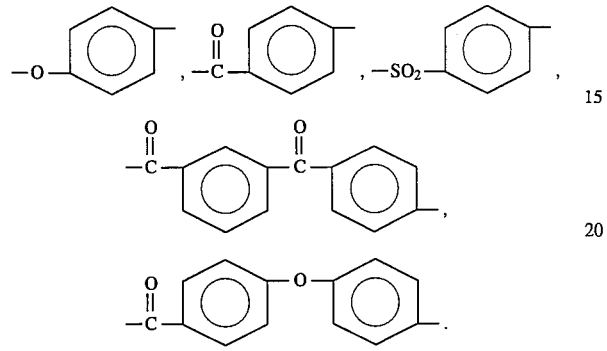

The best results were obtained with 3,5-diamino-4'-phenylethynylbenzophenone.

Figure 2:
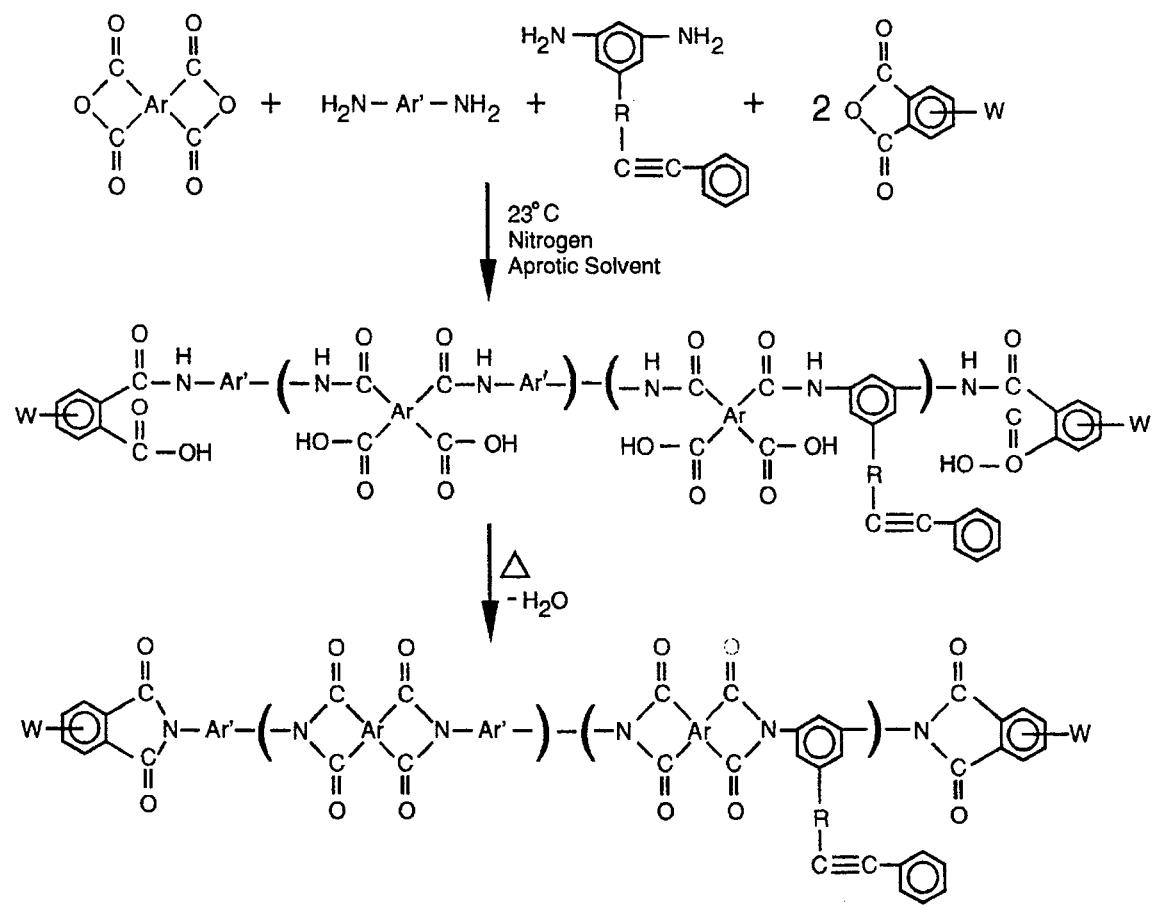
FIG. 2 is a schematic of the synthesis of controlled molecular weight amide acid and imide co-oligomers containing pendent phenylethynyl groups chain terminated with nonreactive or reactive phthalic anhydride based encapping agents according to the present invention.

Controlled molecular weight amide acid and imide co-oligomers containing pendent phenylethynyl groups and chain terminated with either nonreactive or reactive phthalic anhydride based endcapping agents were prepared according to FIG. 2. The chemical structures of these oligomers are indicated below:

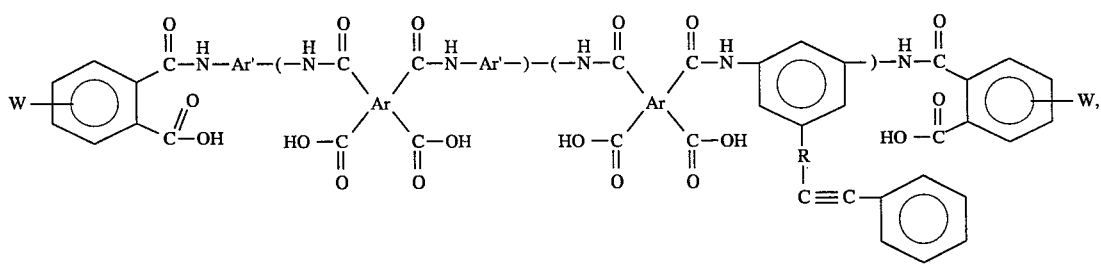

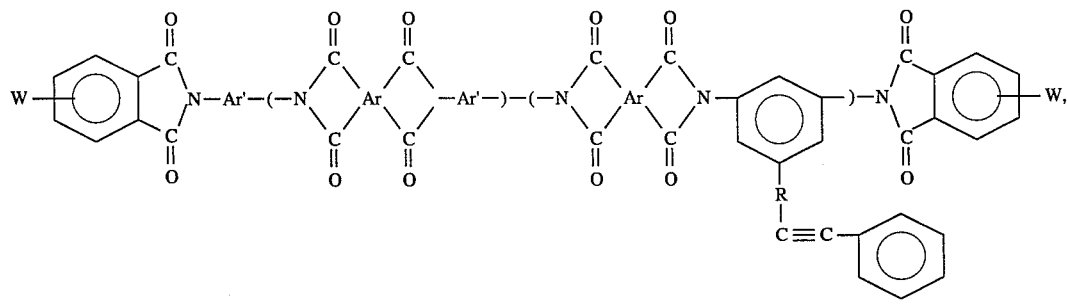

wherein Ar' is a member selected from the group consisting of:

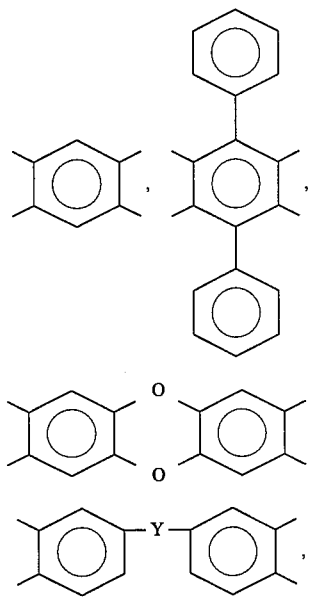

wherein Y is a bond or Y is a radical selected from the group consisting of: O, CO, $SO_2$, $C(CF_3)_2$, isophthalpyl, terephthaloyl, 1,3-diphenoxy and 1,4-diphenoxy.

wherein Ar is a member selected from the group consisting of:

wherein the catenation is selected from the group consisting of 2,2'; 2,3'; 2,4'; 3,3'; 3,4'; and 4,4' and X is a bond or X is a radical selected from the group consisting of:

CH₂, O, CO, CH(OH), C(CF₃)₂,

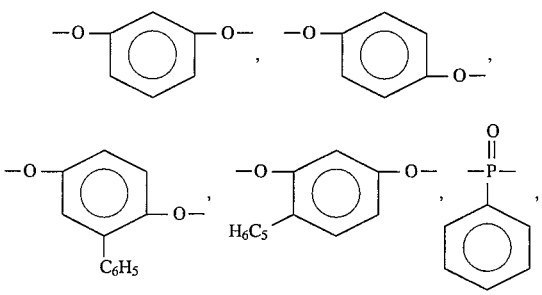

wherein W is a radical selected from the group consisting of:
H,

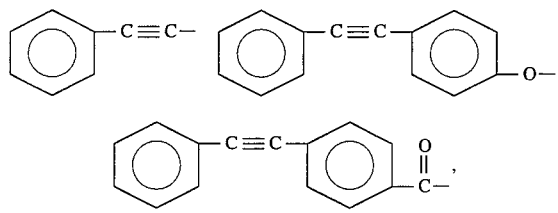

wherein R is a radical selected from the group consisting of:

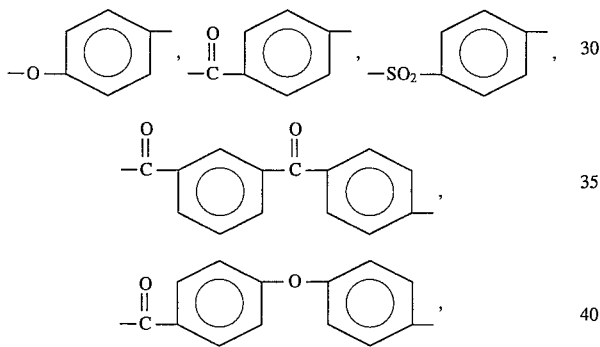

wherein the amount of diamine containing pendent phenylethynyl groups ranges from 1–9 mole %.

Particularly good results were obtained with examples 2, 8 and 13. Polymer characterization is presented in Table 1, thin film mechanical properties are presented in Table 2, adhesive properties are presented in Table 3 and carbon fiber reinforced composite properties are presented in Table 4.

TABLE 1

Imide Oligomers of $\bar{M}_n$(calcd = 5000 g/mol) containing pendant phenylethynyl groups

| Imide Oligo-mer[1] | $\eta_{inh}$,dL/g[2] (Amide acid) | $\eta_{inh}$[3] dLg (Imide) | $T_{gi}(T_m)$,[4] °C. | $T_{gc}$, °C. | 5% Wt. Loss in air[5] initial | 5% Wt. Loss in air[5] cured |
|---|---|---|---|---|---|---|
| 1 | 0.85 | — | ND[6] | 300 (TMA) | — | 465 |
| 2 | 0.33 | — | 240 | 279 | 446 | 493 |
| 3 | 0.65 | — | 265 | 297 | 458 | 476 |
| 4 | 0.32 | 0.28 | 217 (276) | 255 (369) | 451 | 487 |
| 5 | 0.31 | 0.22 | 230 (272, 286) | 293 | 436 | 451 |
| 6 | 0.26 | 0.24 | 209 (278) | 300 | 478 | — |
| 7 | — | 0.29 | 224 | 283 | 496 | 496 |

TABLE 1-continued

Imide Oligomers of $\bar{M}_n$(calcd = 5000 g/mol) containing pendant phenylethynyl groups

| Imide Oligo-mer[1] | $\eta_{inh}$,dL/g[2] (Amide acid) | $\eta_{inh}$[3] dLg (Imide) | $T_{gi}(T_m)$,[4] °C. | $T_{gc}$, °C. | 5% Wt. Loss in air[5] initial | 5% Wt. Loss in air[5] cured |
|---|---|---|---|---|---|---|
| 8 | 0.32 | 0.28 | 231 (282) | 313 | 465 | 532 |
| 9 | 0.21 | 0.41 | 223 (274) | 310 | 463 | 502 |
| 10 | 0.28 | — | 269 | 296 | 451 | 487 |
| 11 | 0.36 | — | ND | ND | 446 | 481 |
| 12 | 0.30 | — | ND | 260 | 447 | 487 |
| 13 | 0.29 | 0.32 | 224 (284) | 289 | 499 | 511 |
| 14 | 0.35 | 0.26 | (243, 262) | 310 | 499 | 460 |
| 15 | 0.33 | 0.31 | 231 | 299 | 490 | 464 |
| 16 | 0.22 | — | ND | ND | 402 | — |
| 17 | 0.31 | — | ND | ND | 413 | — |

[1]Number corresponds to Example number
[2]Determined on 0.5% (w/v) NMP solutions of the amide acid at 25° C.
[3]Determined on 0.5% (w/v) m-cresol solutions of the imide at 25° C.
[4]Determined by DSC at 20° C./min. i = as-isolated oligomer, c = cured sealed DSC pan/350° C./1 h
[5]Determined by TGA at 2.5° C./min
[6]ND: not detected

TABLE 2

Unoriented Thin film tensile properties of Imide Oligomers of $\bar{M}_n$(calcd) = 5000 g/mol containing pendant phenylethynyl groups

| Imide[1] | $T_g$, °C.[2] | Test Temp., °C. | Strength, ksi | Modulus, ksi | Elongation at Break, % |
|---|---|---|---|---|---|
| 2 | — | 23 | 21.8 | 600 | 4 |
|  |  | 177 | 14.0 | 411 | 5 |
|  |  | 200 | 12.0 | 372 | 6 |
| 5 | 289 | 23 | 23.5 | 563 | 8 |
|  |  | 177 | 12.7 | 370 | 6 |
|  |  | 200 | 12.2 | 370 | 9 |
| 7 | 290 | 23 | 18.9 | 495 | 12 |
|  |  | 177 | 10.8 | 301 | 34 |
|  |  | 200 | 9.2 | 276 | 25 |
| 8 | — | 23 | 20.2 | 497 | 10 |
|  |  | 177 | 11.4 | 322 | 9 |
|  |  | 200 | 9.9 | 267 | 17 |
| 9 | 306 | 23 | 20.5 | 495 | 20 |
|  |  | 177 | 12.1 | 296 | 27 |
|  |  | 200 | 10.7 | 299 | 30 |
| 13 | 301 | 23 | 20.4 | 492 | 15 |
|  |  | 177 | 11.2 | 307 | 24 |
|  |  | 200 | 9.9 | 285 | 28 |
| 14 | 294 | 23 | 19.8 | 489 | 12 |
|  |  | 177 | 10.7 | 290 | 11 |
|  |  | 200 | 10.3 | 329 | 11 |
| 15 | 296 | 23 | 19.5 | 457 | 16 |
|  |  | 177 | 10.1 | 291 | 20 |
|  |  | 200 | 9.2 | 299 | 12 |

[1]Number corresponds to Example number.
[2]Determined by DSC at 20°C./min on film samples cured at 100, 225, 350° C. for 1 h each in flowing air.

TABLE 3

PRELIMINARY Ti-to-Ti
TENSILE SHEAR PROPERTIES

| Test Temp., °C. | Strength, MPa | Cohesive Failure, % |
|---|---|---|
| 0.85 3,4'-ODA/0.15 DPEB/BPDP/PA (Example 2) PASA Jell 107 Surface Treatment | | |
| 23 | 3900 | 60 |
| 177 | 4100 | 60 |

TABLE 3-continued

PRELIMINARY Ti-to-Ti TENSILE SHEAR PROPERTIES 0.85 3,4'-ODA/0.15 DPEB/BPDP/PA (Example 2)
Chromic Acid Anodized (5 V) Surface Treatment

| | | |
|---|---|---|
| 23 | 4300 | 75 |
| 177 | 4100 | 75 |

*Processing conditions: 200 psi/300° C./0.5 h, then 200 psi/350° C./1 h 0.70 3,4'-ODA/0.15 APB/0.15 DPEB/BPDA/PEPA
(Example 13)
PASA Jell 107 Surface Treatment

| Processing Conditions | Test Temperature, °C. | Strength, psi | Failure, % |
|---|---|---|---|
| 350° C./200 psi/1 h | 23 | 5000 | 50 C |
| 371° C./200 psi/1 h | 23 | 4800 | 60 C |
| 350° C./100 psi/1 h | 23 | 5200 | 65 C |
| 350° C./200 psi/1 h | 177 | 5000 | 75 C |
| 350° C./100 psi/1 h | 177 | 4500 | 100 C |
| 350° C./200 psi/1 h | 200 | 4700 | 90 C |
| 350° C./200 psi/1 h | 232 | 4000 | 100 C |

0.85 3,4'-ODA/0.15 DPEB/BPDA/PEPA (Example 8)

PASA JELL

| | | | |
|---|---|---|---|
| 371° C./50 psi/1 h | 23 | 2500 | 85 A |
| 371° C./100 psi/1 h | 23 | 3100 | 60 A |
| 371° C./200 psi/1 h | 23 | 3000 | 100 A |
| 1. 300° C./200 psi/0.5 h 2. 350° C./200 psi/1.0 h | 23 | 4000 | |
| Chromic Acid Anod. (5 V) 350° C./200 psi/1 h | 200 | 5000 | 80 A |

TABLE 4

PRELIMINARY COMPOSITE PROPERTIES[1]

| Imide Oligomer[2] | Property | Layup | Test Temp., °C. | Value |
|---|---|---|---|---|
| 2 | Flexural Strength, ksi | Unidirectional | 23 | 260.3 |
| | | | 177 | 219.4 |
| | Flexural Modulus, Msi | | 23 | 21.5 |
| | | | 177 | 20.6 |
| 2 | Open Hole Compression, ksi | (42/50/8) | 23 | 57.5 |
| | | | 177 (wet) | 44.6 |
| 2 | Compression (IITRI) Strength, ksi | Unidirectional | 23 | 232 |
| | | | 177 | 224 |
| | Modulus, Msi | | 23 | 23.1 |
| | | | 177 | 22.0 |
| 2 | Tensile Strength, ksi | Unidirectional | 23 | 358.8 |
| | Tensile Modulus, Msi | | 23 | 23.7 |
| | Poission's Ratio | | 23 | 0.33 |
| 2 | Short Beam Shear Strength, ksi | Unidirectional | 23 | 13.5 |
| | | | 150 | 11.2 |
| | | | 177 | 10.6 |
| | | | 204 | 8.8 |
| 8 | Flexural Strength, ksi | Unidirectional | 23 | 233.5 |
| | | | 177 | 190.3 |
| 8 | Flexural Modulus, msi | Unidirectional | 23 | 21.08 |
| | | | 177 | 18.73 |

[1]Composite cured 1 h at 371° C./200 psi, solution coated IM-7 carbon graphite fibers
[2]Number corresponds to Example number.

Figure 3:
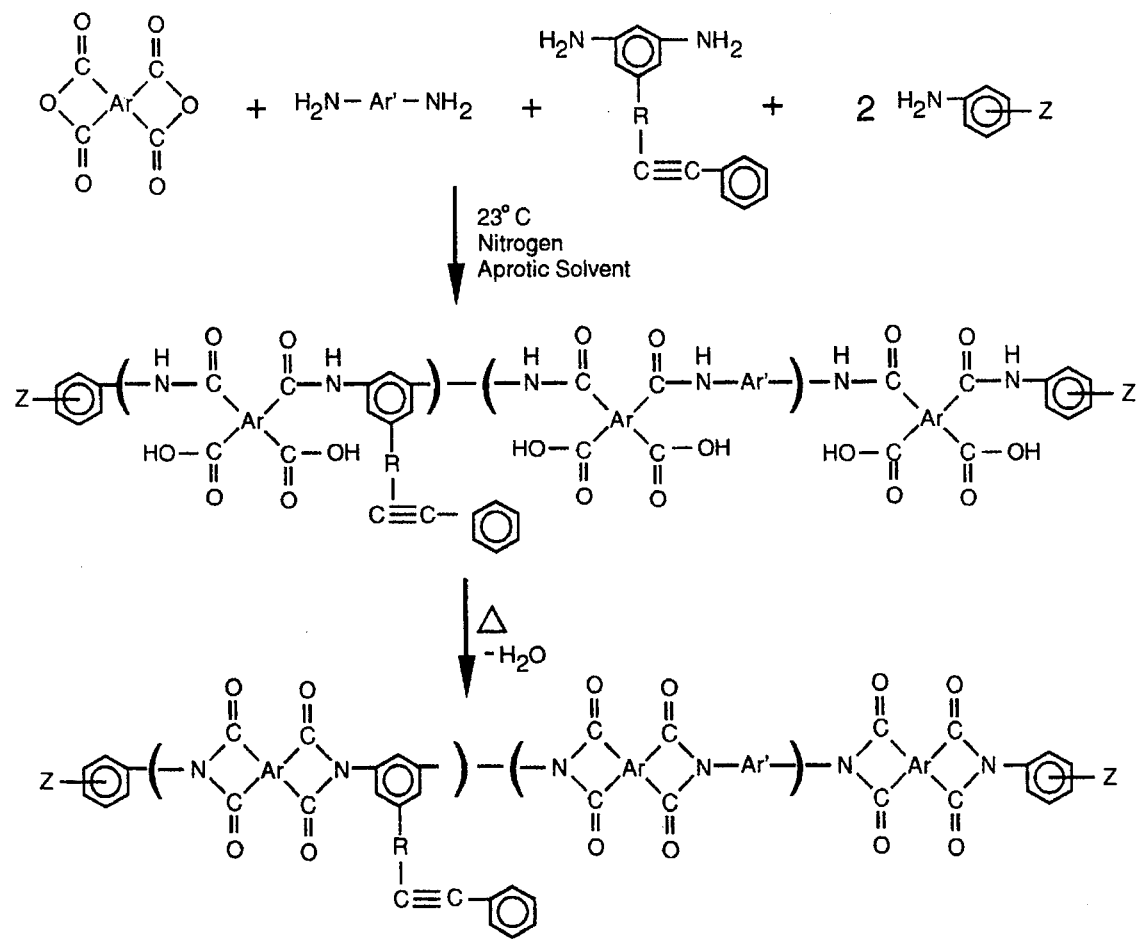
FIG. 3 is a schematic of the synthesis of controlled molecular weight amide acid and imide co-oligomers containing pendent phenylethynyl groups chain terminated with nonreactive or reactive aniline based encapping agents according to the present invention.

Controlled molecular weight amide acid and imide co-oligomers containing pendent phenylethynyl groups and chain terminated with either nonreactive or reactive aniline based endcapping agents were prepared according to FIG. 3. The chemical structures of these oligomers are indicated below:

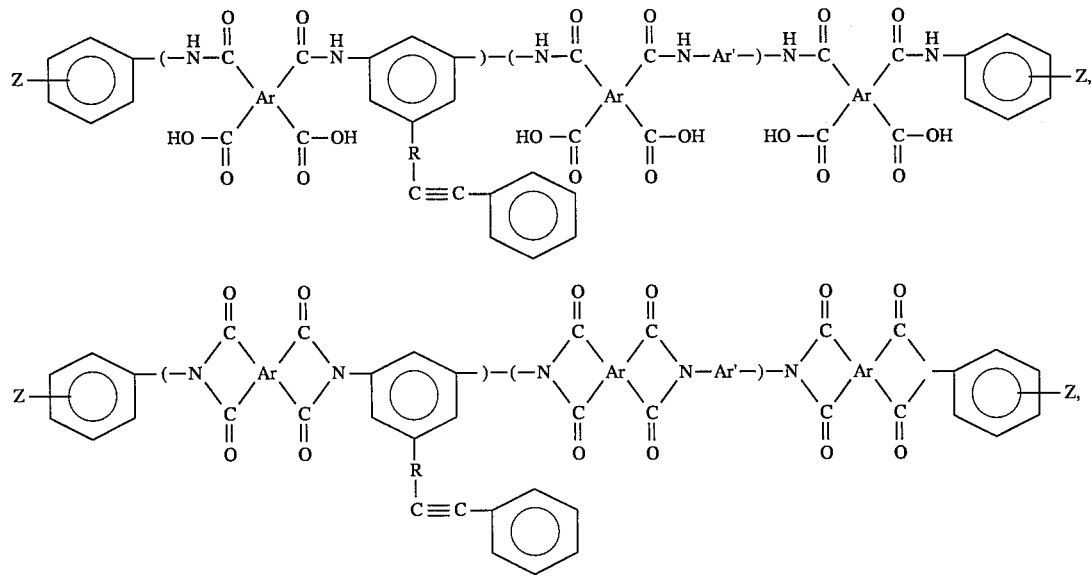

wherein Ar is a member selected from the group consisting of:

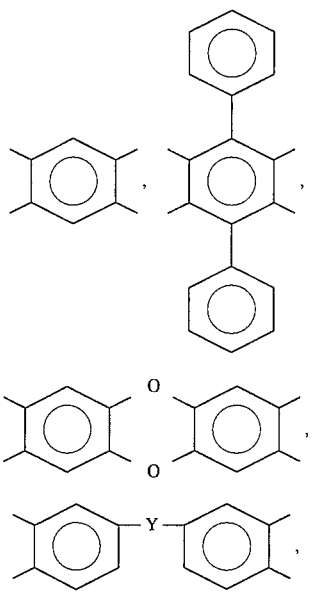

wherein Y is a bond or Y is a radical selected from the group consisting of: O, CO, $SO_2$, $C(CF_3)_2$, isophthalpyl, terephthaloyl, 1,3-diphenoxy and 1,4-diphenoxy.

wherein Ar' is a member selected from the group consisting of:

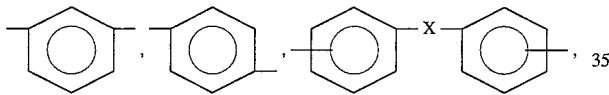

wherein the catenation is selected from the group consisting of 2,2'; 2,3'; 2,4'; 3,3'; 3,4'; and 4,4' and X is a bond or X is a radical selected from the group consisting of:

$CH_2$, O, CO, CH(OH), $C(CF_3)_2$

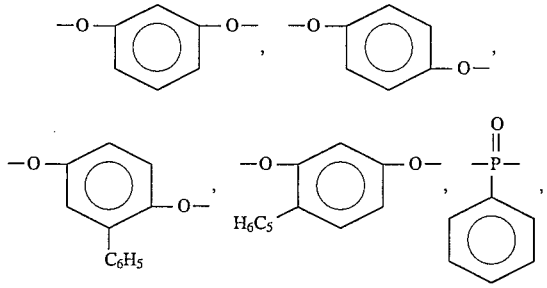

wherein Z is a radical selected from the group consisting of: H,

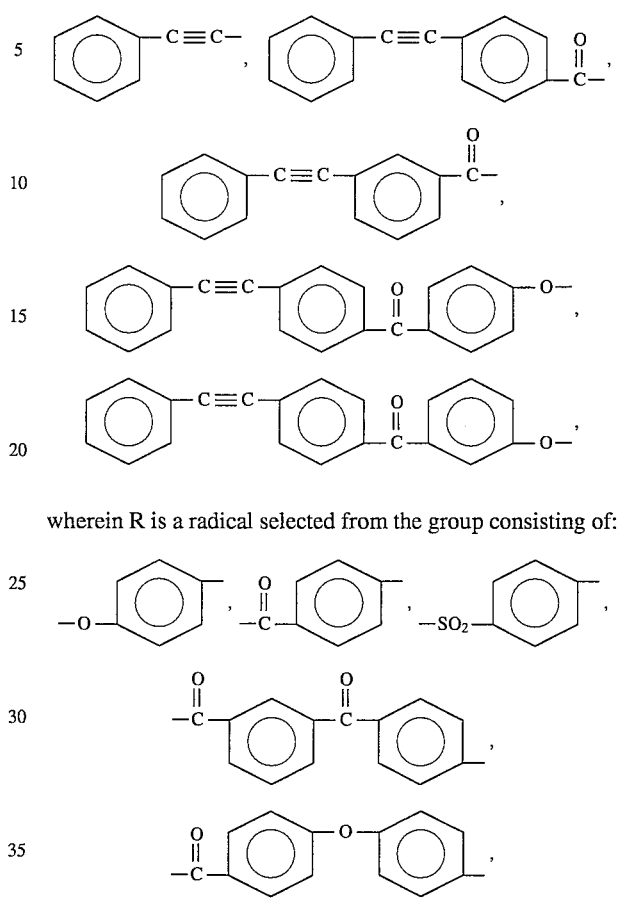

wherein R is a radical selected from the group consisting of:

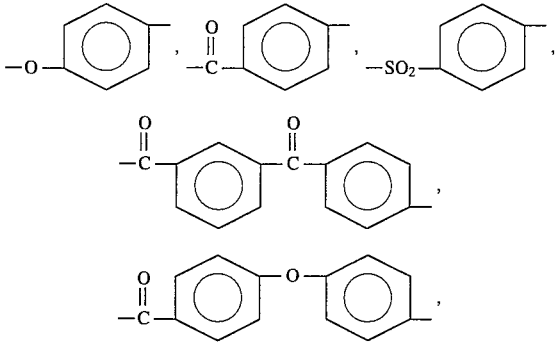

wherein the amount of diamine containing pendent phenylethynyl groups ranges from 1–99 mole %.

The best results were obtained from example 6. Polymer characterization is presented in Table 1.

Figure 4:
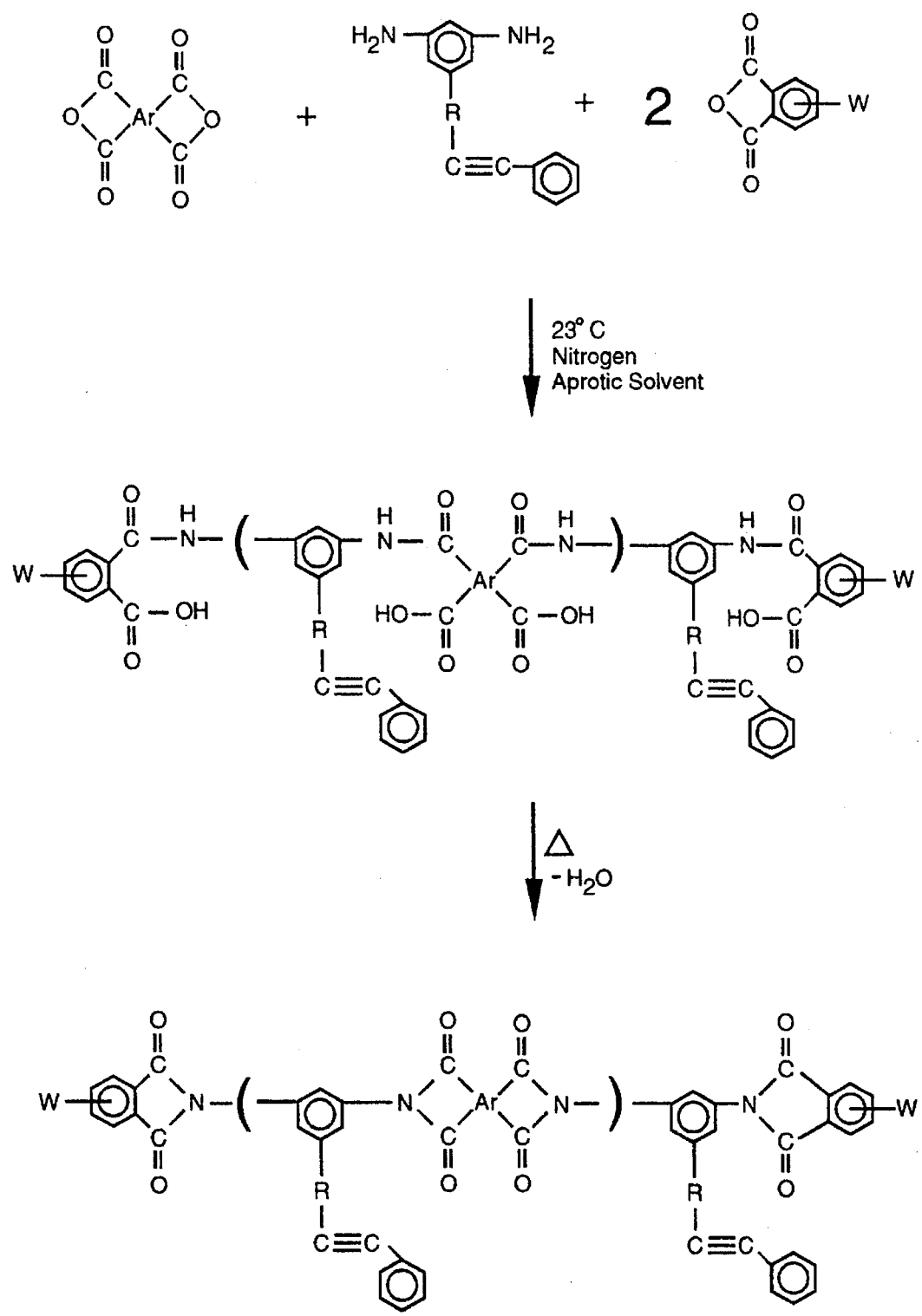
FIG. 4 is a schematic of the synthesis of controlled molecular weight amide acid and imide oligomers containing pendent phenylethynyl groups chain terminated with nonreactive or reactive phthalic anhydride based encapping agents according to the present invention.

Controlled molecular weight amide acid and imide oligomers containing pendent phenylethynyl groups and chain terminated with either nonreactive or reactive phthalic anhydride based endcapping agents were prepared according to FIG. 4. The chemical structures of these oligomers are indicated below:

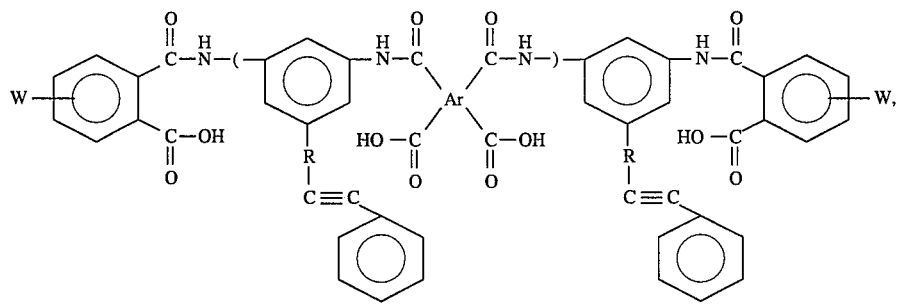

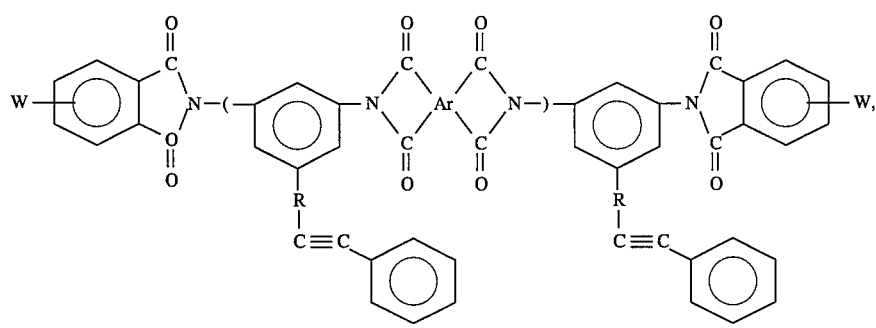

wherein Ar is a member selected from the group consisting of:

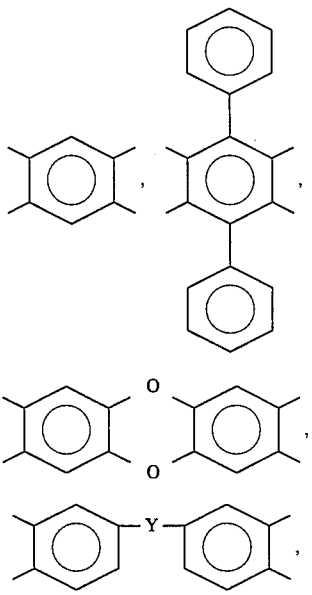

wherein Y is a bond or Y is a radical selected from the group consisting of: O, CO, $SO_2$, $C(CF_3)_2$, isophthalpyl, terephthaloyl, 1,3-diphenoxy and 1,4-diphenoxy.

wherein W is a radical selected from the group consisting of: H,

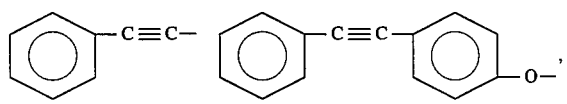

-continued

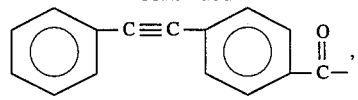

wherein R is a radical selected from the group consisting of:

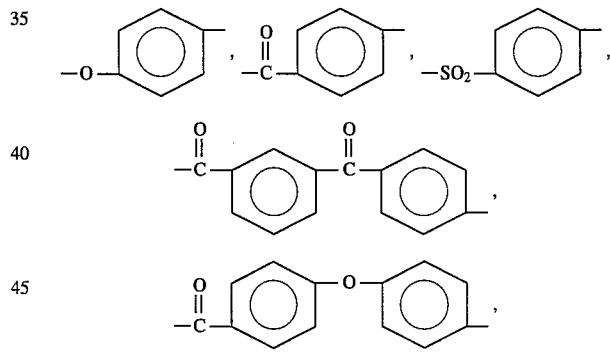

The best results were obtained with example 17. Polymer characterization is presented in Table 1.

Figure 5:
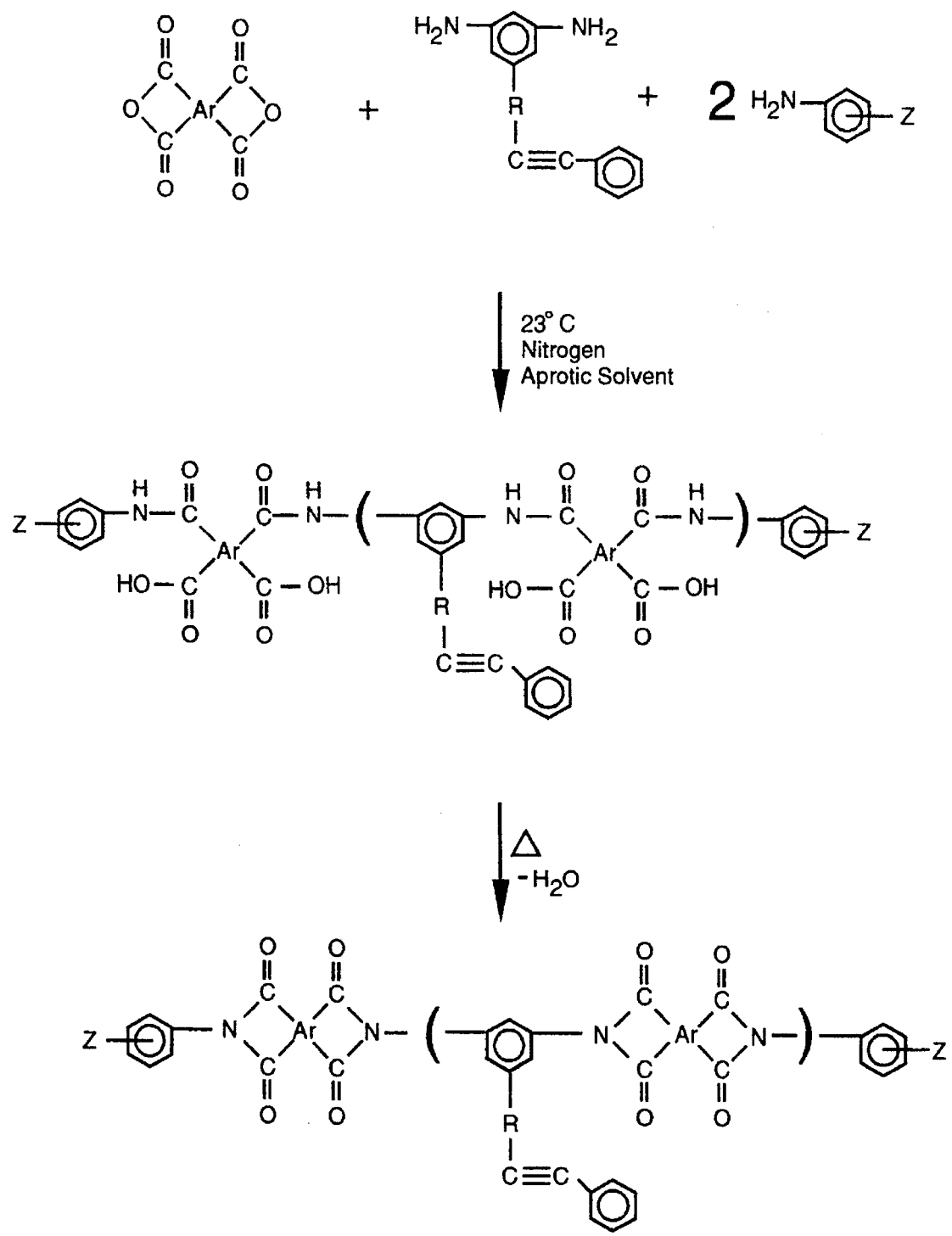
FIG. 5 is a schematic of the synthesis controlled molecular weight amide acid and imide oligomers containing pendent phenylethynyl groups chain terminated with nonreactive or reactive aniline based encapping agents according to the present invention.

Controlled molecular weight amide acid and imide oligomers containing pendent phenylethynyl groups and chain terminated with either nonreactive or reactive aniline based endcapping agents were prepared according to FIG. 5. The chemical structures of these oligomers are indicated below:

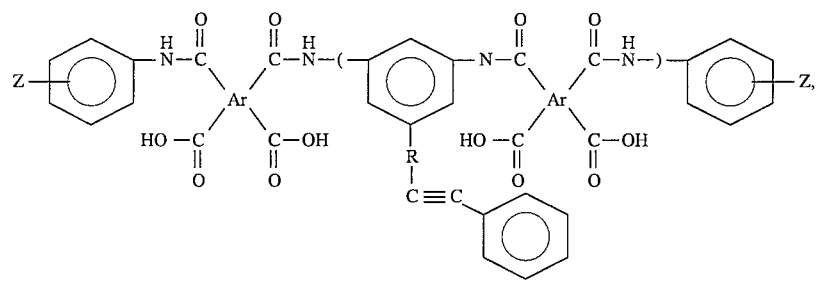

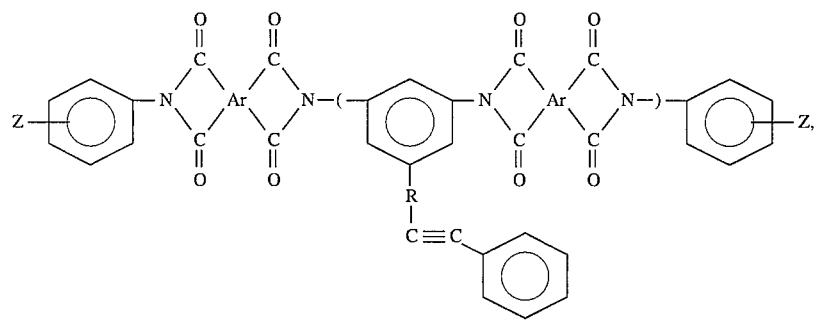

wherein Ar is a member selected from the group consisting of:

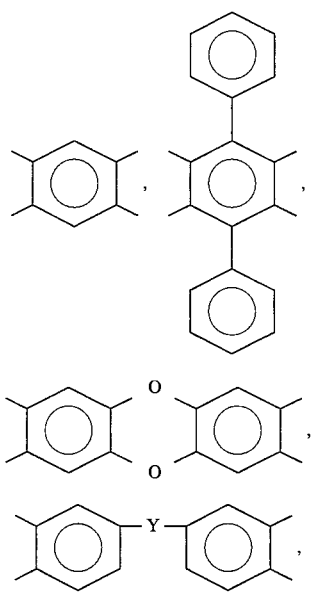

wherein Y is a bond or Y is a radical selected from the group consisting of: O, CO, $SO_2$, $C(CF_3)_2$, isophthalpyl, terephthaloyl, 1,3-diphenoxy and 1,4-diphenoxy.

wherein Ar' is a member selected from the group consisting of:

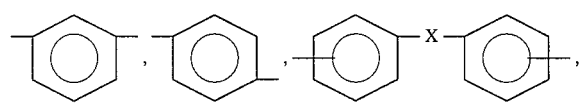

wherein Z is a radical selected from the group consisting of:
H,

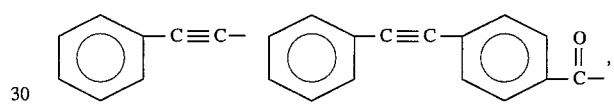

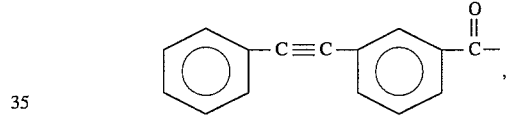

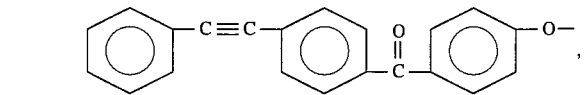

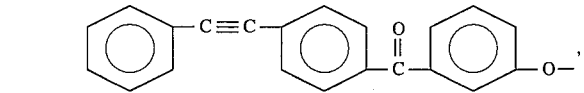

wherein R is a radical selected from the group consisting of:

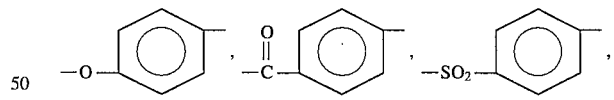

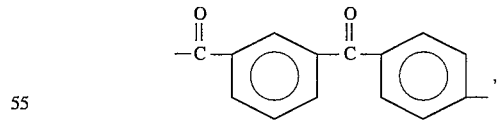

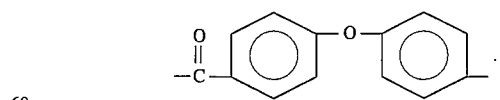

The best results were obtained with example 16. Polymer characterization is presented in Table 1.

Figure 6:
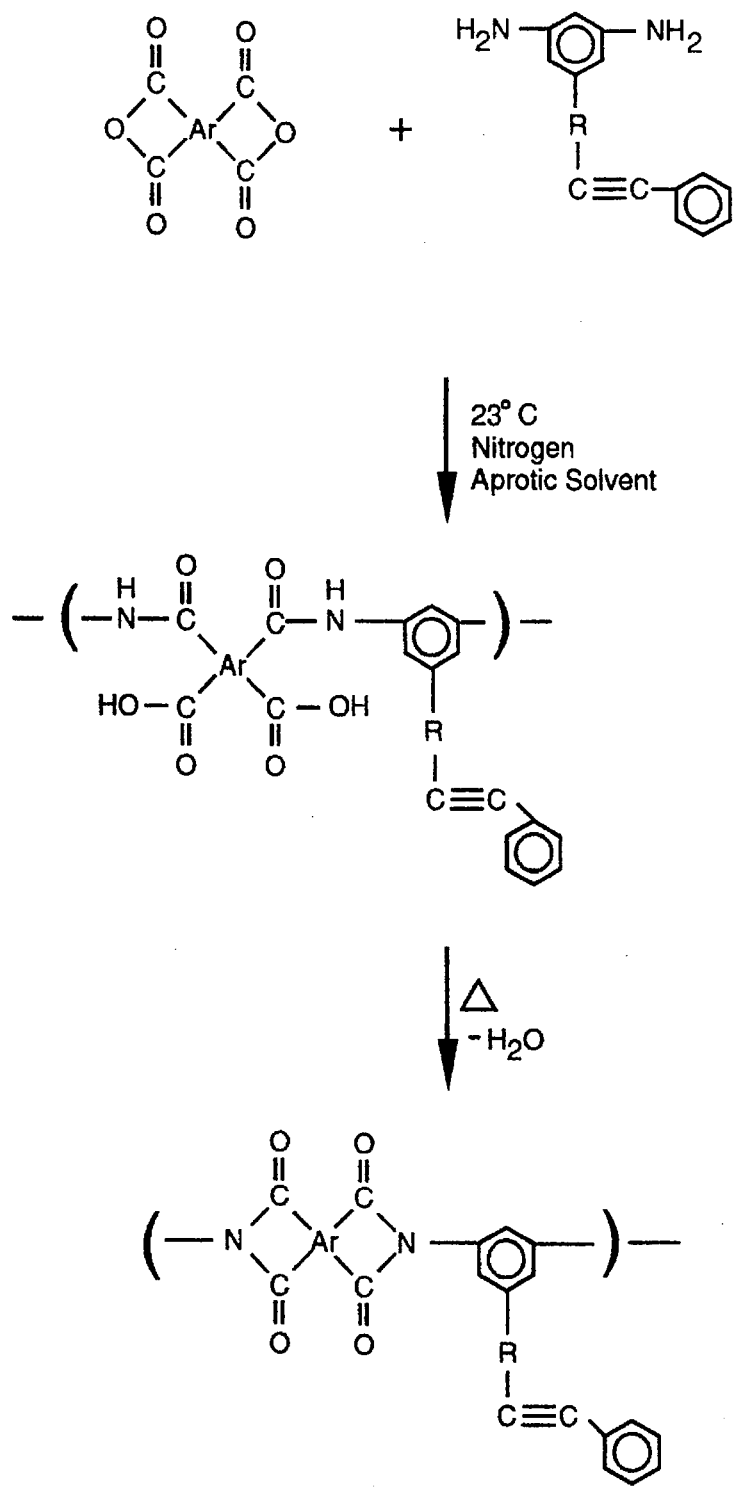
FIG. 6 is the reaction sequence for preparation of uncontrolled molecular weight polyimide containing pendent phenylethynyl groups where R is a 4-benzoyl group and Ar is 3,3+4,4'-diphenylether.

Unendcapped, uncontrolled molecular weight poly(amide acid)s and polyimides containing pendent phenylethynyl groups were prepared according to FIG. 6. The chemical structures of the polymers are indicated below:

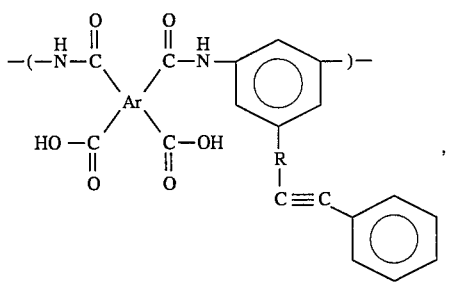

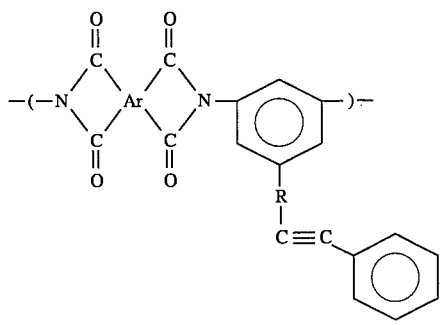

wherein Ar is a member selected from the group consisting of:

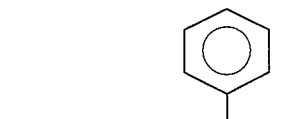

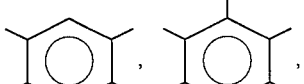

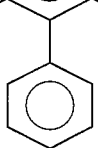

wherein Y is a bond or Y is a radical selected from the group consisting of: O, CO, SO$_2$, C(CF$_3$)$_2$, isophthalpyl, terephthaloyl, 1,3-diphenoxy and 1,4-diphenoxy.

wherein R is a radical selected from the group consisting of:

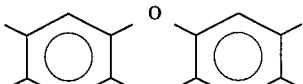

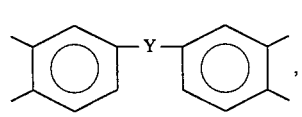

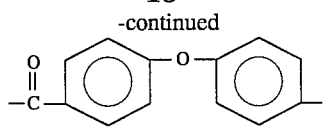

The best results were obtained from example 1. Polymer characterization is presented in Table 1.

Having generally described the invention, a more complete understanding thereof can be obtained by reference to the following examples which are provided herein for purposes of illustration only and do not limit the invention.

Diamine Synthesis

The following example illustrates the reaction sequence in FIG. 1 for the preparation of the diamine, 3,5-diamino-4'-phenylethynylbenzophenone.

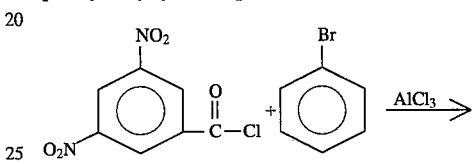

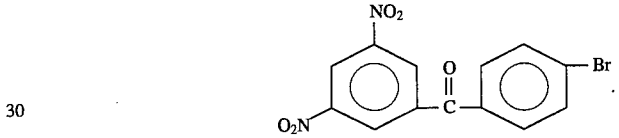

3,5-Dinitro-4'-bromobenzophenone

To a flame dried 3 necked 3 L round bottom flask equipped with nitrogen inlet, thermometer, mechanical stirrer, condenser and acid trap was charged 3,5-dinitrobenzoyl chloride (99.00 g, 0.429 mol) and bromobenzene (2000 mL). Anhydrous aluminum chloride (73.40 g, 0.550 mol) was added as a powder in several portions over a 40 minute period at ambient temperature. Once the addition of aluminum chloride was complete, the temperature was increased to ~65° C. and maintained for ~24 h. The solution was cooled to ambient temperature and added to a rapidly stirred acidic solution (hydrochloric acid 500 mL and 6600 mL distilled water/ice). A yellow tacky solid separated from solution and was recovered by vacuum filtration. The tacky solid was washed with methanol, recovered by vacuum filtration and dried at 100° C. for 2 h in flowing air to afford 107.60 g (71%) of a yellow solid. The crude solid was recrystallized from toluene to afford 90.1 g (60%) of a yellow crystalline solid, mp (DSC, 10° C./min)=179° C. Anal. calcd. for C$_{13}$H$_7$N$_2$O$_5$Br: C, 44.47%; H, 2.00%; N, 7.98%; Br, 22.75%; Found: C, 44.26%; H, 1.75%; N 8.06%; Br, 22.98%.

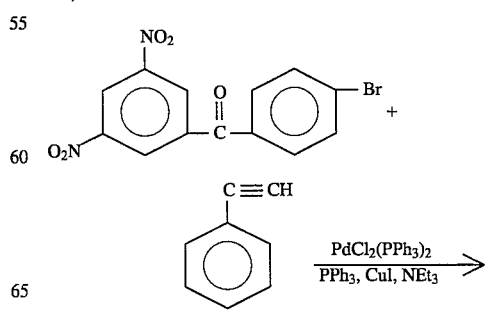

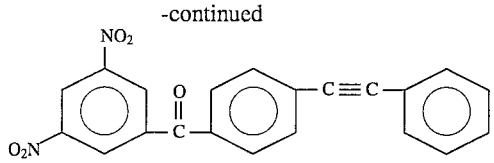

3,5-Dinitro-4'-phenylethynylbenzophenone

To a flame dried 3 necked 2 L round bottom flask equipped with nitrogen inlet, thermometer, mechanical stirrer and condenser was charged 3,5-dinitro-4'-bromobenzophenone (101.0 g, 0.288 mol), triethylamine (1 L), cuprous iodide (0.24 g, 1.26 mmol), triphenylphosphine (1.50 g, 5.72 mmol), bis(triphenylphosphine)palladium dichloride (0.30 g, 0.4274 mmol) and phenylacetylene (32.32 g, 0.316 mol). The temperature was increased to 85° C. and maintained for ~12 h. After ~2 hr, the solid precipitate was very thick making stirring difficult. The mixture was cooled to ambient temperature and the crude solid recovered by vacuum filtration. The solid was washed successively in acidic water, distilled water and dried at 105° C. in a forced air oven for ~17 h to afford 104 g (97%) of a dark brown powder, (DSC, 10° C./min) very small peak at 156° C. and a broad peak centered at 181° C. The onset of the exothermic peak maximum was 403° C. and 423° C., respectively. Recrystallization from toluene (1 L) afforded a first crop of yellow/orange crystals (66 g, 63%) with a sharp melting point centered at 188° C. A second crop of crystals (15.0 g) was obtained after reducing the volume of the filtrate, mp 188° C. Final yield was 83.5 g (78%). Anal. calcd. for $C_{21}H_{12}N_2O_5$: C, 67.73%; H, 3.25%; N, 7.52%; Found: C, 67.64%; H, 3.55%; N 7.67%.

orange solution was cooled to ~10°–15° C. by means of an ice bath. A cooled solution (~10° C.) of stannous chloride dihydrate (78.4 g, 0.35 mol) in concentrated hydrochloric acid (300 mL) was added dropwise while maintaining the temperature between 10°–20° C. After the addition, the ice bath was removed and the reaction mixture allowed to warm to room temperature. The mixture was stirred at room temperature for ~16 h. During this time the product precipitated from solution. The solid was collected, placed in distilled water and neutralized with aqueous ammonium hydroxide. The crude material was collected by filtration, washed in water and dried at 65° C. for 1 h in flowing air to afford 16.0 g (98%) of a crude solid. The crude product was recrystallized form toluene to afford 13.1 g (80%) of a yellow powder, mp (DSC, 10° C./min) 156° C. Anal. calcd. for $C_{21}H_{16}N_2O$: C, 80.74%; H, 5.16%; N, 8.97%; Found: C, 80.73%; H, 5.10%; N 8.98%.

EXAMPLE 1

1.0 3,5-Diamino-4'-phenylethynylbenzophenone and 1.0 4,4'-Oxydiphthalic Anhydride with no Endcapping Agent The following example illustrates the reaction sequence in FIG. 6 for the preparation of the uncontrolled high molecular weight PEPI where R is a 4-benzoyl group and Ar is 3,3',4,4'-diphenylether and the monomer stoichiometry is 1.0 to 1.0.

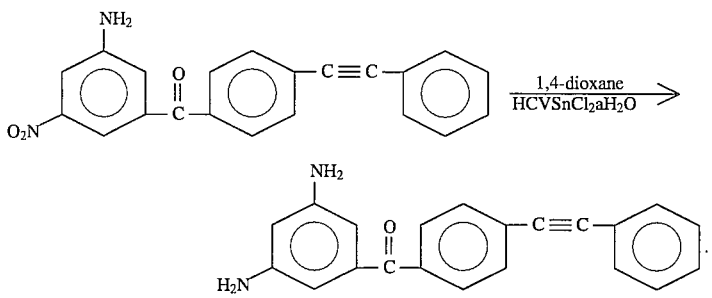

3,5-Diamino-4'-phenylethynylbenzophenone

To a 1 L Erlenmeyer flask equipped with a magnetic stirrer was charged 3,5-dinitro-4'-phenylethynylbenzophenone (19.6 g, 0.053 mol) and 1,4-dioxane (450 mL). The

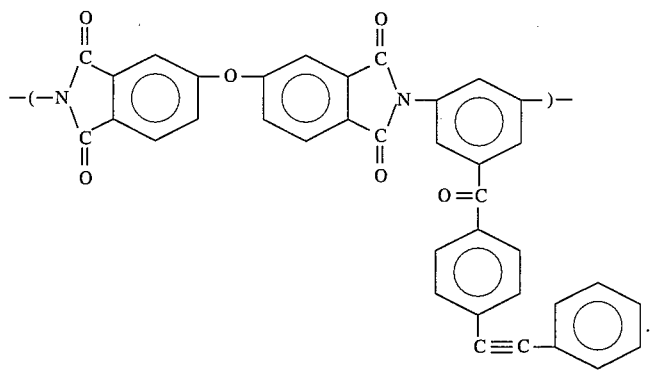

Into a flame dried 100 mL three necked round bottom flask equipped with nitrogen inlet, mechanical stirrer, and drying tube were placed 3,5-diamino-4'-phenylethynylbenzophenone (2.0069 g, 0.0064 mol) and 6 mL of N,N-dimethylacetamide (DMAc). After dissolution, 4,4'-oxydiphthalic anhydride (1.9931 g, 0.0064 mol) and DMAc (10 mL) were added to give a final concentration of 20.0% (w/w) solution. The reaction was stirred at room temperature for 24 h under nitrogen. The inherent viscosity of the poly(amide acid) solution (0.5% in DMAc at 25° C.) was 0.85 dL/g. Approximately 7 g of poly(amide acid) solution was used to cast an unoriented thin film. Toluene (30 mL) was added to the remaining poly(amide acid) solution and the temperature increased and maintained at ~150° C. for ~16 h under a nitrogen atmosphere. As cyclodehydration to the imide occurred, the polymer precipitated. The polyimide powder was washed in hot water, warm methanol, and dried under vacuum at 230° C. for 4 h to provide a tan powder (2.3 g, 43% yield). The $T_g$ of the uncured as-isolated polymer (DSC, 20° C./min) was 273° C. and the exothermic onset and peak occurred at 340° C. and 419° C., respectively. The $T_g$ of the cured polymer (cure conditions: 350° C./1 h/sealed pan) was not detectable by DSC. Unoriented thin film cast from the DMAc solution of the poly(amide acid) and cured at 100°, 225°, and 350° C. for 1 h each in flowing air did not exhibit a $T_g$ by DSC. The $T_g$ by thermomechanical analysis (TMA) at a heating rate of 5° C./min was 300° C. Polymer characterization is presented in Table 1.

EXAMPLE 2

0.85:0.15 3,4'-Oxydianiline and 3,5-Diamino-4'-phenylethynylbenzophenone, and 0.9093 3,3',4,4'-Biphenyltetracarboxylic Dianhydride, Using 9.07 mole % Stoichiometric offset and 18.14 mole % Phthalic Anhydride (Calculated $(\overline{M})_n$=5000 g/mol The following example illustrates the reaction sequence in FIG. 2 for the preparation of the controlled molecular weight PEPI where Ar' is 3,4'-diphenylether and R is a 4-benzoyl group and Ar is 3,3',4,4'-biphenyl and W is a hydrogen atom. The ratio of diamines [Ar':R] is 0.85:0.15. The stoichiometric imbalance is 9.07 mole % and the endcapping reagent is 18.14 mole % of phthalic anhydride.

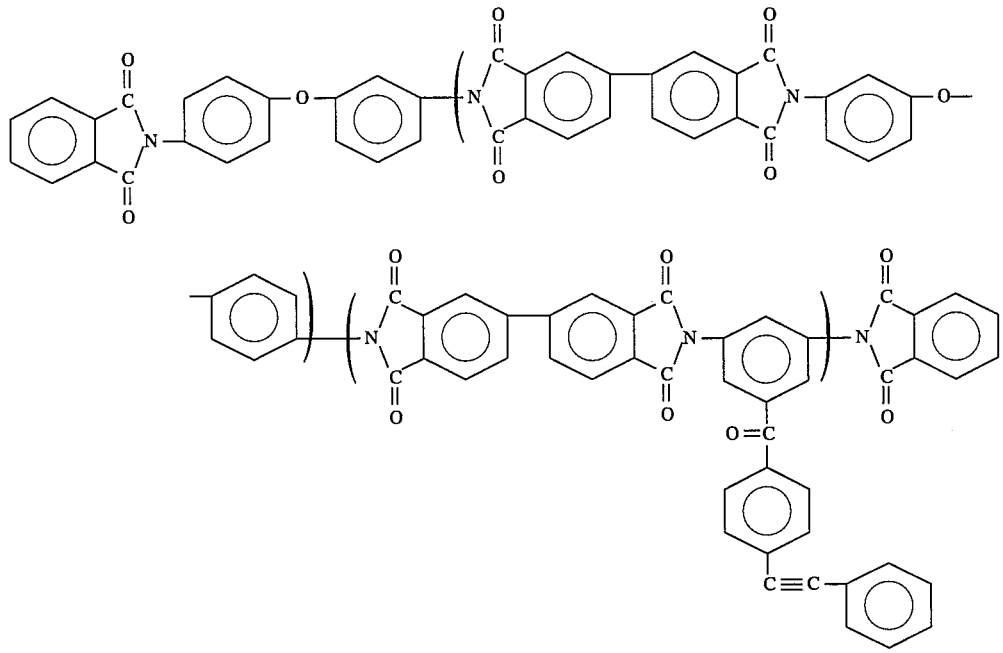

Into a flame dried 100 mL three necked round bottom flask equipped with nitrogen inlet, mechanical stirrer, and drying tube were placed 3,4'-oxydianiline (3.7220 g, 0.0186 mol), 3,5-diamino-4'-phenylethynylbenzophenone (1.0246 g, 0.0033 mol) and 9 mL N-methyl-2-pyrrolidinone (NMP). After dissolution, a slurry of 4,4'-biphenyltetracarboxylic dianhydride, (5.8502 g, 0.0199 mol), and phthalic anhydride (0.5924 g, 0.0040 mol) in 10 mL of NMP was added and washed in with an additional 7 mL of NMP to afford a 30.0% (w/w) solution. The reaction was stirred at room temperature for 24 h under nitrogen. The inherent viscosity of the amide acid oligomeric solution (0.5% in NMP at 25° C.) was 0.33 dL/g. Approximately 11 g of amide acid oligomeric solution was used to cast an unoriented thin film. The reaction vessel was fitted with a moisture trap and toluene (40 mL) was added to the remaining amide acid oligomeric solution and the temperature increased and maintained at ~180° C. for ~16 h under a nitrogen atmosphere. As cyclodehydration to the imide occurred, the oligomer began to precipitate. The oligomer was washed in hot water, warm methanol, and dried under vacuum at 230° C. for 4 h to provide a brown powder (6.9 g, 66% yield). The $T_g$ of the uncured as-isolated oligomer (DSC, 20° C./min) was 240° C. with a very slight $T_m$ at 325° C. and the exothermic onset and peak occurred at 340° C. and 423° C., respectively. The $T_g$ of the cured polymer (cure conditions: 350° C./1 h/sealed pan) was not detected by DSC. Unoriented thin films cast from a NMP solution of the amide acid oligomer cured at 100°, 225°, and 350° C. for 1 h each in flowing air gave tensile strength, tensile modulus, and elongation at 23° C. of 21.8 ksi, 600 ksi, and 4% and at 177° C. of 14.0 ksi, 411 ksi, and 5% and at 200° C. of 12 ksi, 372 ksi, and 6%, respectively. The $T_g$ of the cured film was 279° C. A sample compression molded at 300° C./200 psi/0.5 h then 350° C./200 psi/1 h had a $G_{IC}$ (critical strain energy release rate) of 6.2 in lb/in² and a $T_g$ of 280° C. The titanium (Ti) to Ti tensile shear properties bonded at 300° C./200 psi/0.5 h then 350° C./200 psi/1 h were 3900 at 23° C. and 4100 at 177° C. Flexural properties of composite panels prepared from prepreg of example 2 on IM-7 fiber processed at 250° C./50 psi/1 h then 371° C./200 psi/1 h with a unidirectional lay-up gave flexural strength and flexural modulus at 23° C. of 260.3 ksi and 21.52 Msi and at 177° C. of 219.4 ksi and 20.58 Msi, respectively. Polymer characterization is presented in Table 1, thin film mechanical properties are presented in Table 2, adhesive properties are presented in Table 3 and carbon fiber reinforced composite properties are presented in Table 4.

EXAMPLE 3

0.85:0.15 3,4'-Oxydianiline and 3,5-Diamino-4'-phenylethynylbenzophenone, and 0.976 3,3',4,4'-Biphenyltetracarboxylic Dianhydride, Using 2.4 mole % Stoichiometric offset and 4.8 mole % Phthalic Anhydride (Calculated $(\overline{M})_n$=20,000 g/mole)

The following example illustrates the reaction sequence in FIG. 2 for the preparation of the controlled molecular weight PEPI where Ar' is 3,4'-diphenylether and R is a 4-benzoyl group and Ar is 3,3',4,4'-biphenyl and W is a hydrogen atom. The ratio of diamines [Ar':R] is 0.85:0.15. The stoichiometric imbalance is 2.4 mole % and the endcapping reagent is 4.8 mole % of phthalic anhydride.

wash in the solid to afford a 30.0% (w/w) solution. The reaction was stirred at room temperature for 24 h under nitrogen. The inherent viscosity of the amide acid oligomeric solution (0.5% in NMP at 25° C.) was 0.645 dL/g. Approximately 7.1 g of amide acid oligomeric solution was used to cast an unoriented thin film. The reaction vessel was fitted with a moisture trap and toluene (40 mL) was added to the remaining amide acid oligomeric solution and the temperature increased and maintained at ~180° C. for ~16 h under a nitrogen atmosphere. As cyclodehydration to the imide occurred, the oligomer began to precipitate. The oligomer was washed in hot water, warm methanol, and dried under vacuum at 230° C. for 4 h to provide a brown powder (6.0 g, 75% yield). The $T_g$ of the uncured as-isolated oligomer (DSC, 20° C./min) was 265° C. and the exothermic onset and peak occurred at 340° C. and 423° C., respectively. The $T_g$ of the cured polymer (cure conditions: 350° C./1 h/sealed pan) was 297° C. by DSC. Unoriented thin films cast from a NMP solution of the amide acid oligomer cured at 100°, 225°, and 350° C. for 1 h each in flowing air gave tensile strength, tensile modulus, and elongation at 23° C. of 16.3 ksi, 473 ksi, and 4%. The $T_g$ of the cured film was not detectable by DSC. Polymer characterization is presented in Table 1.

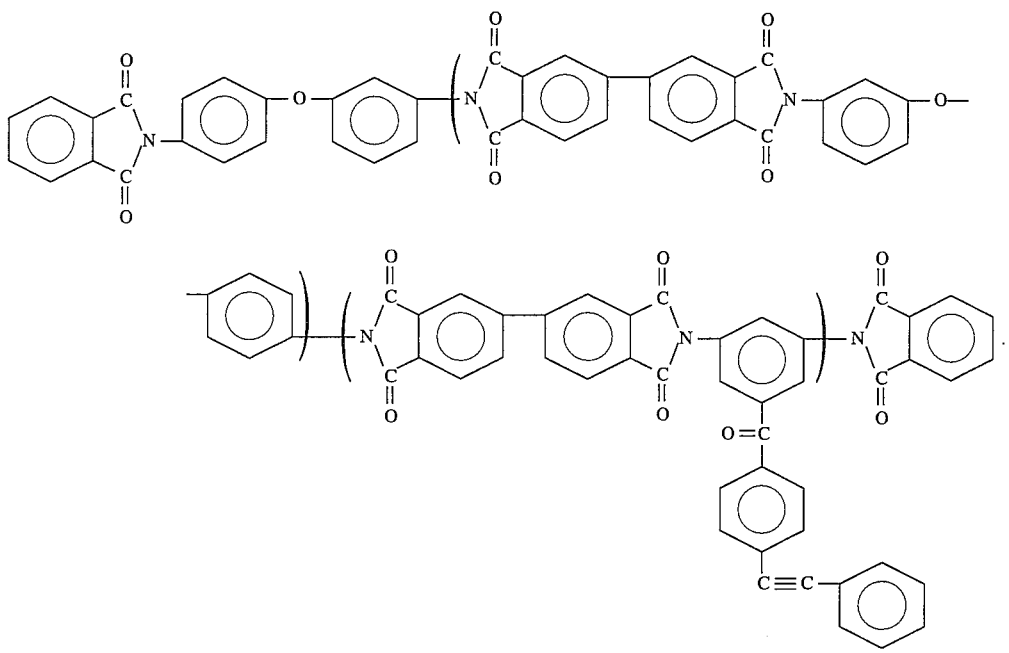

Into a flame dried 100 mL three necked round bottom flask equipped with nitrogen inlet, mechanical stirrer, and drying tube were placed 3,4'-oxydianiline (2.8765 g, 0.01436 mol), 3,5-diamino-4'-phenylethynylbenzophenone (0.7919 g, 0.00253 mol) and 10.1 mL N-methyl-2-pyrrolidinone (NMP). After dissolution, 4,4'-biphenyltetracarboxylic dianhydride, (4.8530 g, 0.0165 mol), and phthalic anhydride (0.1201 g, 0.00081 mol). NMP (10.0 mL) was used to

EXAMPLE 4

0.90:0.10 3,4'-Oxydianiline and
3,5-Diamino-4'-phenylethynylbenzophenone, and
0.9093 3,3',4,4'-Biphenyltetracarboxylic
Dianhydride, Using 9.07 mole % Stoichiometric
offset and 18.14 mole % Phthalic Anhydride
(Calculated $(\overline{M})_n$=5000 g/mole)

The following example illustrates the reaction sequence in FIG. 2 for the preparation of the controlled molecular weight PEPI where Ar' is 3,4'-diphenylether and R is a 4-benzoyl group and Ar is 3,3',4,4'-biphenyl and W is a hydrogen atom. The ratio of diamines [Ar':R] is 0.90:0.10. The stoichiometric imbalance is 8.97 mole % and the endcapping reagent is 17.94 mole % of phthalic anhydride.

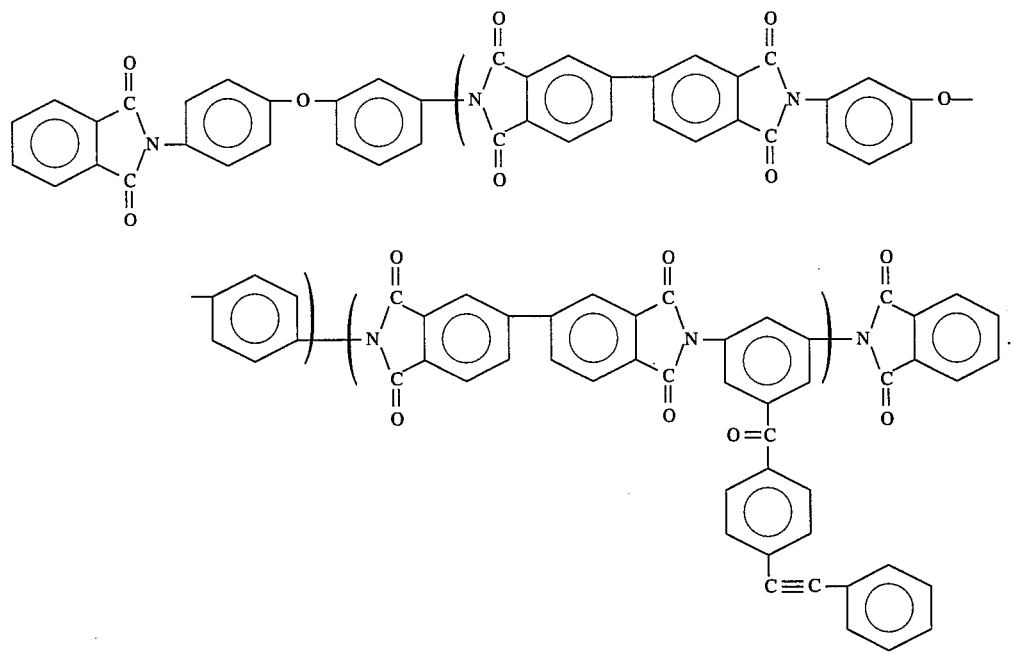

Into a flame dried 100 mL three necked round bottom flask equipped with nitrogen inlet, mechanical stirrer, and drying tube were placed 3,4'-oxydianiline (4.8752 g, 0.0243 mol), 3,5-diamino-4'-phenylethynylbenzophenone (0.8450 g, 0.0027 mol) and 10 mL N-methyl-2-pyrrolidinone (NMP). After dissolution, a slurry of 4,4'-biphenyltetracarboxylic dianhydride (7.2451 g, 0.0246 mol) and phthalic anhydride (0.7188 g, 0.0049 mol) in 10 mL of NMP was added and washed in with an additional 10 mL of NMP to afford a 30.6% (w/w) solution. The reaction was stirred at room temperature for 24 h under nitrogen. The inherent viscosity of the amide acid oligomeric solution (0.5% in NMP at 25° C.) was 0.32 dL/g. Approximately 13 g of amide acid oligomeric solution was used to cast an unoriented thin film. The reaction vessel was fitted with a moisture trap and toluene (60 mL) was added to the remaining amide acid oligomeric solution and the temperature increased and maintained at ~180° C. for ~16 h under a nitrogen atmosphere. As cyclodehydration to the imide occurred, the oligomer began to precipitate. The oligomer was washed in hot water, warm methanol, and dried under vacuum at 230° C. for 4 h to provide a yellow powder (8.91 g, 70% yield). The inherent viscosity of the imide oligomer (0.5% in m-cresol at 25° C.) was 0.28 dL/g. The $T_g$ of the uncured as-isolated oligomer (DSC, 20° C./min) was 217° C. with a $T_m$ at 276° C. The $T_g$ of the cured polymer (cure conditions: 350° C./1 h/sealed pan) was 255° C. with a $T_m$ at 369° C. The $T_g$ of the cured film was 259° C. with a $T_m$ at 367° C. Polymer characterization is presented in Table 1.

EXAMPLE 5

0.70:0.30 3,4'-Oxydianiline and
3,5-Diamino-4'-phenylethynylbenzophenone, and
0.9093 3,3',4,4'-Biphenyltetracarboxylic
Dianhydride Using 9.07 mole % Stoichiometric
offset and 18.14 mole % Phthalic Anhydride
(Calculated $(\overline{M})_n$=5000 g/mole)

The following example illustrates the reaction sequence in FIG. 2 for the preparation of the controlled molecular weight PEPI where Ar' is 3,4'-diphenylether and R is a 4-benzoyl group and Ar is 3,3',4,4'-biphenyl and W is a hydrogen atom. The ratio of diamines [Ar':R] is 0.70:0.30. The stoichiometric imbalance is 9.38 mole % and the endcapping reagent is 18.76 mole % of phthalic anhydride.

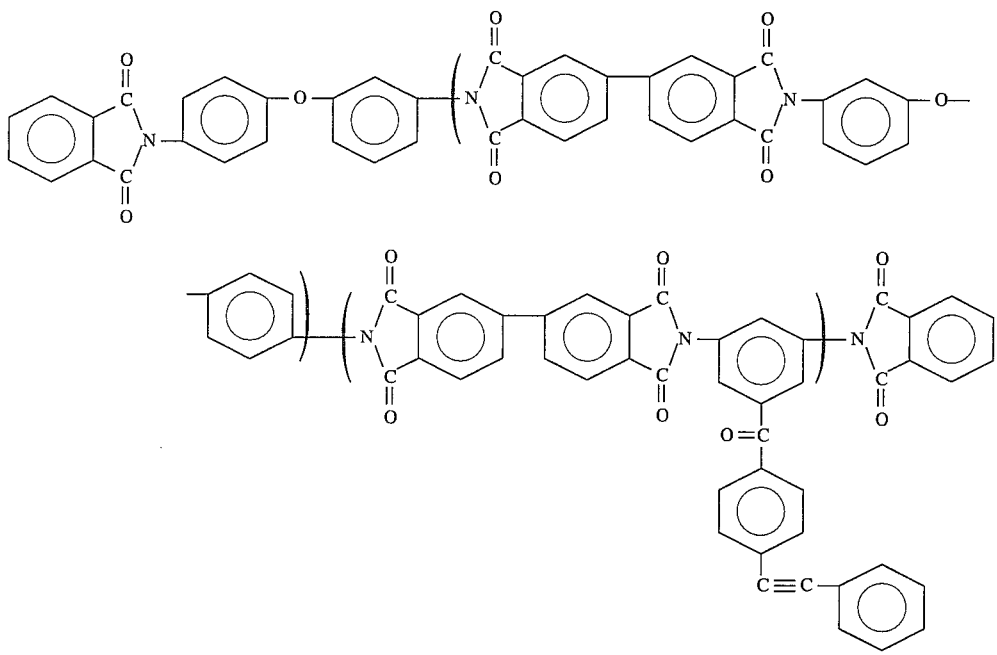

Into a flame dried 100 mL three necked round bottom flask equipped with nitrogen inlet, mechanical stirrer, and drying tube were placed 3,4'-oxydianiline (3.5721 g, 0.0178 mol), 3,5-diamino-4'-phenylethynylbenzophenone (2.3882 g, 0.0076 mol) and 10 mL N-methyl-2-pyrrolidinone (NMP). After dissolution, a slurry of 4,4'-biphenyltetracarboxylic dianhydrides, (6.7947 g, 0.0231 mol), and phthalic anhydride (0.7081 g, 0.0048 mol) in 10 mL of NMP was added and washed in with an additional 10 mL of NMP to afford a 30.3% (w/w) solution. The reaction was stirred at room temperature for 24 h under nitrogen. The inherent viscosity of the amide acid oligomeric solution (0.5% in NMP at 25° C.) was 0.31 dL/g. Approximately 11 g of amide acid oligomeric solution was used to cast an unoriented thin film. The reaction vessel was fitted with a moisture trap and toluene (60 mL) was added to the remaining amide acid oligomeric solution and the temperature increased and maintained at ~180° C. for ~16 h under a nitrogen atmosphere. As cyclodehydration to the imide occurred, the oligomer began to precipitate. The oligomer was washed in hot water, warm methanol, and dried under vacuum at 230° C. for 4 h to provide a brown powder (8.93 g, 71% yield). The inherent viscosity of the imide oligomer (0.5% in m-cresol at 25° C.) was 0.22 dL/g. The $T_g$ of the uncured as-isolated oligomer (DSC, 20° C./min) was 230° C. with $T_m$s at 272° and 286° C. The $T_g$ of the cured polymer (cure conditions: 350° C./1 h/sealed pan) was 293° C. Unoriented thin films cast from a NMP solution of the amide acid oligomer cured at 100°, 225°, and 350° C. for 1 h each in flowing air gave tensile strength, tensile modulus, and elongation at 23° C. of 23.5 ksi, 563 ksi, and 8%; at 177° C. of 12.7 ksi, 370 ksi, and 6% and at 200° C. of 12.2 ksi, 370 ksi, and 9%, respectively. The $T_g$ of the cured film was 289° C. Polymer characterization is presented in Table 1 and thin film mechanical properties are presented in Table 2.

EXAMPLE 6

0.85:0.15 3,4'-Oxydianiline and 3,5-Diamino-4'-phenylethynylbenzophenone, and 3,3',4,4'-Biphenyltetracarboxylic Dianhydride Using 9.07 mole % Stoichiometric offset and 18.14 mole % 3-Aminophenoxy-4'-phenylethynylbenzophenone (Calculated $(\overline{M})_n$=5000 g/mole)

The following example illustrates the reaction sequence in FIG. 3 for the preparation of the controlled molecular weight PEPI where Ar is 3,4'-diphenylether and R is a 4-benzoyl group and Ar is 3,3'-, 4,4'-biphenyl and Z is a phenoxy-4'-phenylethynylbenzophenone group located in the 3 position. The ratio of diamines [Ar':R] is 0.85:0.15. The stoichiometric imbalance is 9.07 mole % and the endcapping reagent is 18.14 mole % of 3-aminophenoxy-4'-phenylethynylbenzophenone.

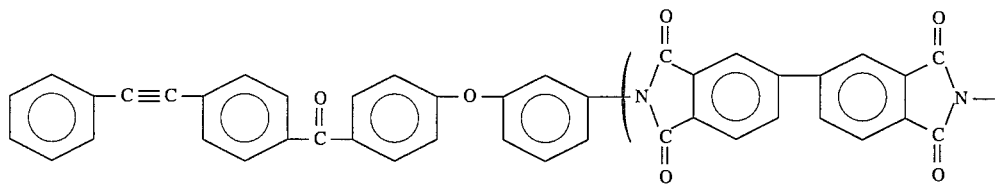

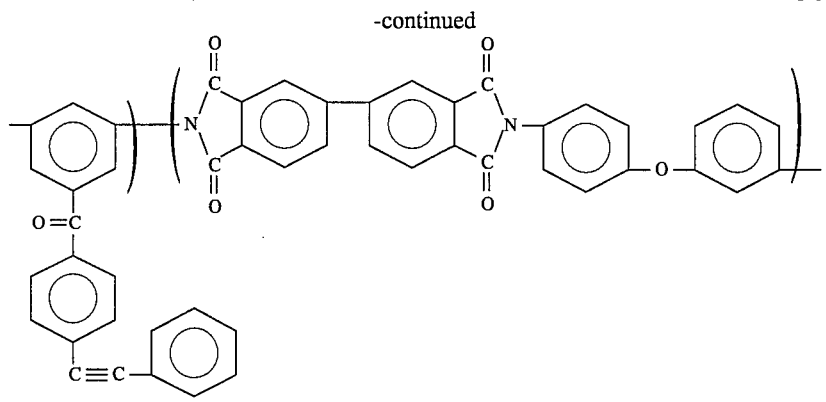

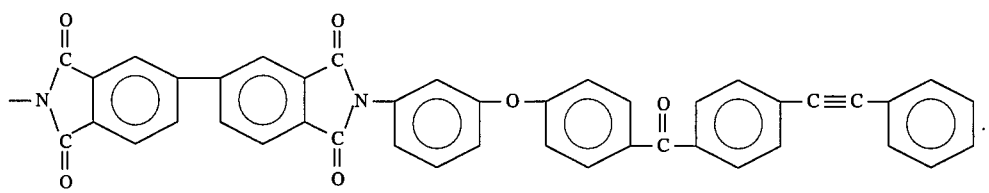

Into a flame dried 100 mL three necked round bottom flask equipped with nitrogen inlet, mechanical stirrer, and drying tube were placed 3,4'-oxydianiline (3.8826 g, 0.0194 mol), 3,5-diamino-4'-phenylethynylbenzophenone (1.0689 g, 0.0034 mol), 3-aminophenoxy-4'phenylethynylbenzophenone (1.7723 g, 0.0046 mol) and 10 mL (39.4% w/w) N-methyl-2-pyrrolidinone (NMP). After dissolution, a slurry of 3,3',4,4'-biphenyltetracarboxylic dianhydride (7.3809 g, 0.0251 mol) in 10 mL (41.7% w/w) of NMP was added and washed in with an additional 11 mL of NMP to afford a 30.6% (w/w) solution. The reaction was stirred at room temperature for 24 h under nitrogen. The inherent viscosity of the amide acid oligomeric solution (0.5% in NMP at 25° C.) was 0.26 dL/g. Approximately 10.85 g of amide acid oligomeric solution was used to cast an unoriented thin film. Toluene (60 mL) was added to the remaining amide acid oligomeric solution and the temperature increased and maintained at ~180° C. for ~16 h under a nitrogen atmosphere. As cyclodehydration to the imide occurred, a precipitate formed. The mixture was cooled, the oligomer was washed in hot water, warm methanol, and dried under vacuum at 220° C. for 1.5 h to provide a tan powder (10.06 g, 76% yield). The inherent viscosity of the imide oligomer (0.5% in m-cresol at 25° C.) was 0.24 dL/g. The $T_g$ of the uncured as-isolated oligomer (DSC, 20° C./min) was 209° C. with a $T_m$ at 278° C. and the exothermic onset and peak occurred at 359° C. and 406° C., respectively. The $T_g$ of the cured polymer (cure conditions: 350° C./1 h/sealed pan) was 300° C. An unoriented thin films cast from a NMP solution of the amide acid oligomer cured at 100°, 225°, and 350° C. for 1 h each in flowing air was phase separated. The $T_g$ of the cured film was 299° C. Polymer characterization is presented in Table 1.

EXAMPLE 7

0.75:0.15:0.10 3,4'-Oxydianiline,
1,3-bis(3-aminophenoxy)benzene and
3,5-Diamino-4'-phenylethynylbenzophenone, and
3,3',4,4'-Biphenyltetracarboxylic Dianhydride,
Using 9.22 mole % Stoichiometric offset and 18.44
mole % 4-Phenylethynylphthalic Anhydride
(Calculated $(\overline{M})_n$=5000 g/mole)

The following example illustrates the reaction sequence in FIG. 2 for the preparation of the controlled molecular weight PEPI where Ar'(1) is 3,4'-diphenylether and Ar'(2) is 1,3-phenoxyphenyl and R is a 4-benzoyl group and Ar is 3,3',4,4'-biphenyl and W is a phenylethynyl group located in the 4 position. The ratio of diamines [Ar' (1):Ar' (2):R] is 0.75:0.15:0.10. The stoichiometric imbalance is 9.22 mole % and the endcapping reagent is 18.44 mole % of 4-phenylethynylphthalic anhydride.

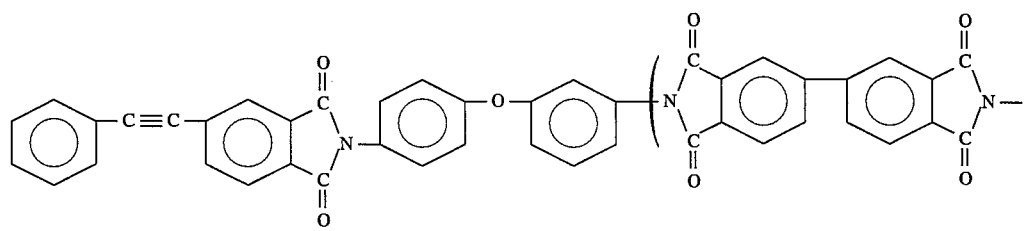

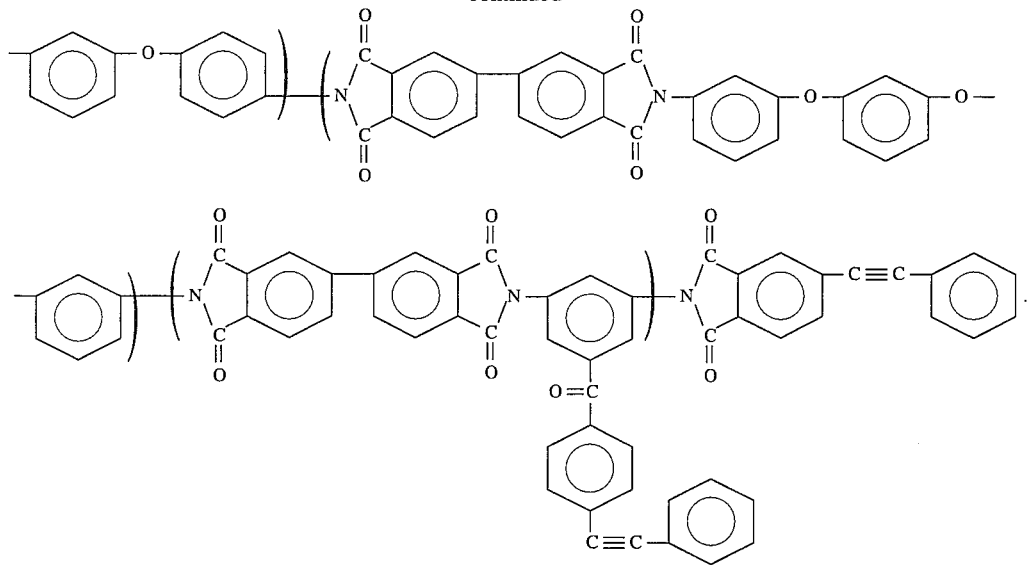

Into a flame dried 100 mL three necked round bottom flask equipped with nitrogen inlet, mechanical stirrer, and drying tube were placed 3,4'-oxydianiline (2.9030 g, 0.0145 mol), 1,3-bis(3-aminophenoxy)benzene (0.8476 g, 0.0029 mol), 3,5-diamino-4'-phenylethynylbenzophenone (0.6038 g, 0.0019 mol) and 20 mL (17.4% w/w) of m-cresol. After dissolution, a slurry of 3,3',4,4'-biphenyltetracarboxylic dianhydride (5.1627 g, 0.0175 mol) and 4-phenylethynylphthalic anhydride (0.8848 g, 0.0036 mol) in 20 mL (22.6% w/w) of m-cresol was added and washed in with an additional 15 mL of m-cresol to afford a 15.5% (w/w) solution. The reaction mixture was stirred at room temperature for ~16 h. The tan opaque solution was warmed to ~100° C. for 0.75 h to effect dissolution of the oligomer. The solution was cooled to ~50° C. and isoquinoline (9 drops) was added to the mixture. The temperature was increased and maintained at ~205° C. for ~6.5 h under a nitrogen atmosphere. The mixture was cooled, the oligomer precipitated in methanol, washed in warm methanol, and dried at 230° C. under vacuum for 1 h to provide a light yellow powder (9.7 g, ~100% yield). The inherent viscosity of a 0.5% (w/v) solution of the imide oligomer in m-cresol at 25° C. was 0.26 dL/g. The $T_g$ of the uncured as-isolated oligomer (DSC, 20° C./min) was 226° C. with an exothermic onset and peak at 359° C. and 425° C., respectively. The $T_g$ of the cured polymer (cure conditions: 350° C./1 h/sealed pan) was 286° C. Unoriented thin films cast from a m-cresol solution of the amide acid oligomer cured at 100°, 225°, and 350° C. for 1 h each in flowing air gave tensile strength, tensile modulus, and elongation at 23° C. of 18.9 ksi, 495 ksi, and 12%; at 177° C. of 10.8 ksi, 301 ksi, and 34%; and at 200° C. of 9.2 ksi, 276 ksi, and 25%, respectively. The $T_g$ of the cured film was 290° C. A sample compression molded at 275° C./200 psi/0.5 h then 350° C./200 psi/1 h had a $G_{IC}$ (critical strain energy release rate) of 10.3 in lb/in². Polymer characterization is presented in Table 1 and thin film mechanical properties are presented in Table 2.

EXAMPLE 8

0.85:0.15 3,4'-Oxydianiline and
3,5-Diamino-4'-phenylethynylbenzophenone, and
3,3',4,4'-Biphenyltetracarboxylic Dianhydride,
Using 9.07 mole % Stoichiometric offset and 18.14
mole % 4-Phenylethynylphthalic Anhydride
(Calculated $(\overline{M})_n$=5000 g/mole)

The following example illustrates the reaction sequence in FIG. 2 for the preparation of the controlled molecular weight PEPI where Ar' is 3,4'-diphenylether and R is a 4-benzoyl group and Ar is 3,3',4,4'-biphenyl and W is a phenylethynyl group located in the 4 position. The ratio of diamines [Ar':R] is 0.85:0.15. The stoichiometric imbalance is 9.07 mole % and the endcapping reagent is 18.14 mole % of 4-phenylethynylphthalic anhydride.

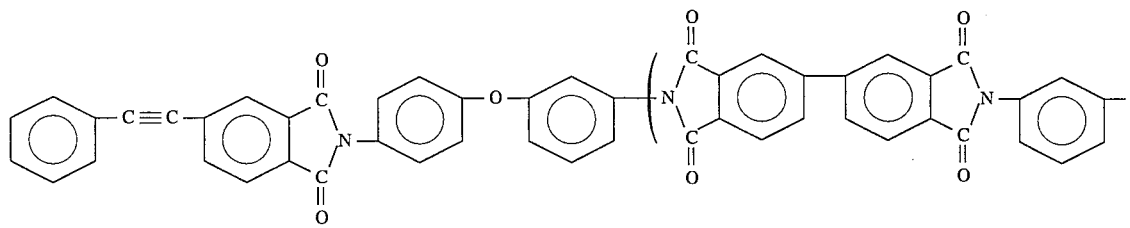

-continued

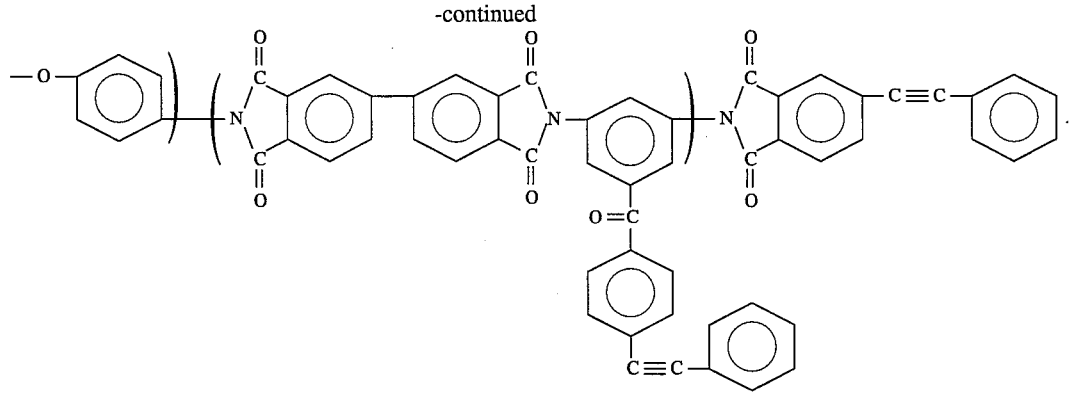

Into a flame dried 100 mL three necked round bottom flask equipped with nitrogen inlet, mechanical stirrer, and drying tube were placed 3,4'-oxydianiline (3.722 g, 0.0186 mol), 3,5-diamino-4'-phenylethynylbenzophenone (1.0246 g, 0.0033 mol) and 8 mL (36.5% w/w) N-methyl-2-pyrrolidinone (NMP). After dissolution, a slurry of 3,3',4,4'-biphenyltetracarboxylic dianhydride (5.8502 g, 0.0199 mol) and 4-phenylethynylphthalic anhydride (0.9847 g, 0.0040 mol) in 9 mL (42.4% w/w) of NMP was added and washed in with an additional 9 mL of NMP to afford a 30.1% (w/w) solution. The reaction was stirred at room temperature for 24 h under nitrogen. The inherent viscosity of the amide acid oligomeric solution (0.5% in NMP at 25° C.) was 0.32 dL/g. Approximately 10 g of amide acid oligomeric solution was used to cast an unoriented thin film. Toluene (60 mL) was added to the remaining amide acid oligomeric solution and the temperature increased and maintained at ~180° C. for ~16 h under a nitrogen atmosphere. As cyclodehydration to the imide occurred, a precipitate formed. The mixture was cooled, the oligomer was washed in hot water, warm methanol, and dried under vacuum at 220° C. for 1.5 h to provide a tan powder (7.94 g, 74% yield). The $T_g$ of the uncured as-isolated oligomer (DSC, 20° C./min) was 226° C. with a $T_m$ at 283° C. and the exothermic onset and peak occurred at 348° C. and 406° C., respectively. The inherent viscosity of the imide oligomer (0.5% in m-cresol at 25° C.) was 0.28 dL/g. The $T_g$ of the cured polymer (cure conditions: 350° C./1 h/sealed pan) was 313° C. Unoriented thin films cast from a NMP solution of the amide acid oligomer cured at 100°, 225°, and 350° C. for 1 h each in flowing air gave tensile strength, tensile modulus, and elongation at 23° C. of 20.2 ksi, 497 ksi, and 10%; at 177° C. of 11.4 ksi, 322 ksi, and 9%, and at 200° C. of 9.9 ksi, 267 ksi, and 17%, respectively. The $T_g$ of the cured film was 318° C. A sample compression molded at 300° C./200 psi/0.5 h then 371° C./200 psi/1 h had a $G_{IC}$ (critical strain energy release rate) of 2.9 in lb/in² and a $T_g$ of 312° C. Flexural properties of composite panels prepared from prepreg of example 8 on IM-7 fiber processed at 250° C./50 psi/1 h then 371° C./200 psi/1 h with a unidirectional lay-up gave flexural strength and flexural modulus at 23° C. of 233.5 ksi and 21.08 Msi and at 177° C. of 190.3 ksi and 18.73 Msi, respectively. Polymer characterization is presented in Table 1, thin film mechanical properties are presented in Table 2, adhesive properties are presented in Table 3 and carbon fiber reinforced composite properties are presented in Table 4.

EXAMPLE 9

0.90:0.10 3,4'-Oxydianiline and
3,5-Diamino-4'-phenylethynylbenzophenone, and
3,3',4,4'-Biphenyltetracarboxylic Dianhydride,
Using 8.97 mole % Stoichiometric offset and 17.94
mole % 4-Phenylethynylphthalic Anhydride
(Calculated $\overline{M}_n$=5000 g/mole)

The following example illustrates the reaction sequence in FIG. 2 for the preparation of the controlled molecular weight PEPI where Ar is 3,4'-diphenylether and R is a 4-benzoyl group and Ar is 3,3',4,4'-biphenyl and W is a phenylethynyl group located in the 4 position. The ratio of diamines [Ar' (1):Ar' (2)] is 0.90:0.10. The stoichiometric imbalance is 8.97 mole % and the endcapping reagent is 17.94 mole % of 4-phenylethynylphthalic anhydride.

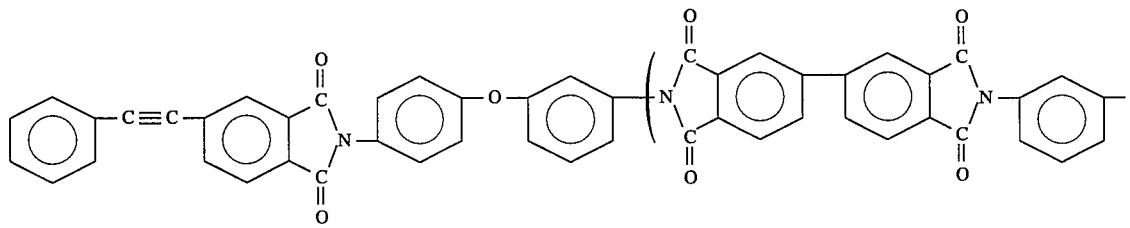

-continued

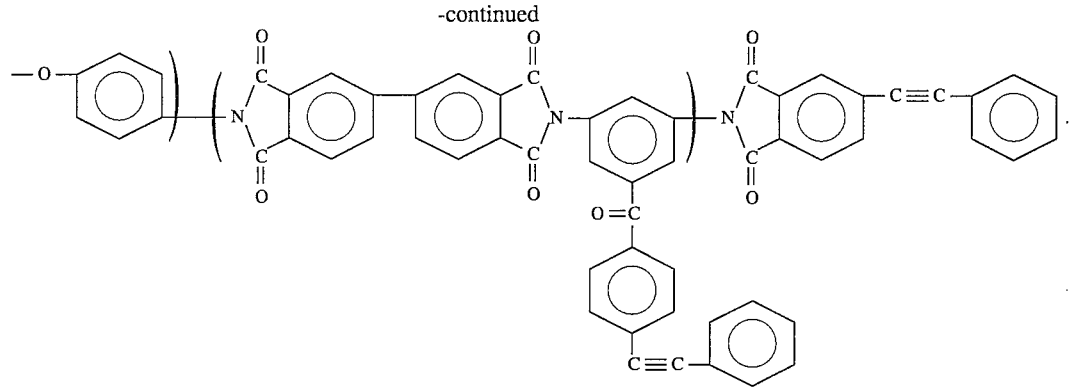

Into a flame dried 100 mL three necked round bottom flask equipped with nitrogen inlet, mechanical stirrer, and drying tube were placed 3,4'-oxydianiline (3.9211 g, 0.0196 mol), 3,5-diamino-4'-phenylethynylbenzophenone (0.6797 g, 0.0022 mol) and 8 mL (35.8% w/w) N-methyl-2-pyrrolidinone (NMP). After dissolution, a slurry of 3,3',4,4'-biphenyltetracarboxylic dianhydride (5.8275 g, 0.0198 mol) and 4-phenylethynylphthalic anhydride (0.9690 g, 0.0040 mol) in 8 mL (45.1% w/w) of NMP was added and washed in with an additional 9 mL of NMP to afford a 30.6% (w/w) solution. The reaction was stirred at room temperature for 24 h under nitrogen. The inherent viscosity of the amide acid oligomeric solution (0.5% in NMP at 25° C.) was 0.21 dL/g. Approximately 10.5 g of amide acid oligomeric solution was used to cast an unoriented thin film. Toluene (60 mL) was added to the remaining amide acid oligomeric solution and the temperature increased and maintained at ~180° C. for ~16 h under a nitrogen atmosphere. As cyclodehydration to the imide occurred, a precipitate formed. The mixture was cooled, the oligomer was washed in hot water, warm methanol, and dried under vacuum at 220° C. for 1.5 h to provide a tan powder (7.00 g, 66% yield). The inherent viscosity of the imide oligomer (0.5% in m-cresol at 25° C.) was 0.41 dL/g. The $T_g$ of the uncured as-isolated oligomer (DSC, 20° C./min) was 223° C. with a $T_m$ at 274° C. and the exothermic onset and peak occurred at 350° C. and 412° C., respectively. The $T_g$ of the cured polymer (cure conditions: 350° C./1 h/sealed pan) was 310° C. Unoriented thin films cast from a NMP solution of the amide acid oligomer cured at 100°, 225°, and 350° C. for 1 h each in flowing air gave tensile strength, tensile modulus, and elongation at 23° C. of 20.5 ksi, 495 ksi, and 20%; at 177° C. of 12.1 ksi, 296 ksi, and 27% and at 200° C. of 10.7 ksi, 299 ksi, and 30%, respectively. The $T_g$ of the cured film was 306° C. Polymer characterization is presented in Table 1 and thin film mechanical properties are presented in Table 2.

EXAMPLE 10

0.90:0.10 3,4'-Oxydianiline and 3,5-Diamino-4'-phenylethynylbenzophenone, and 3,3',4,4'-Benzophenonetetracarboxylic Dianhydride, Using 9.48 mole % Stoichiometric offset and 18.96 mole % 4-Phenylethynylphthalic Anhydride
(Calculated $(\overline{M})_n$=5000 g/mole)

The following example illustrates the reaction sequence in FIG. 2 for the preparation of the controlled molecular weight PEPI where Ar' is 3,4'-diphenylether and R is a 4-benzoyl group and Ar is 3,3',4,4'-benzophenone and W is a phenylethynyl group located in the 4 position. The ratio of diamines [Ar':R] is 0.90:0.10. The stoichiometric imbalance is 9.48 mole % and the endcapping reagent is 18.96 mole % of 4-phenylethynylphthalic anhydride.

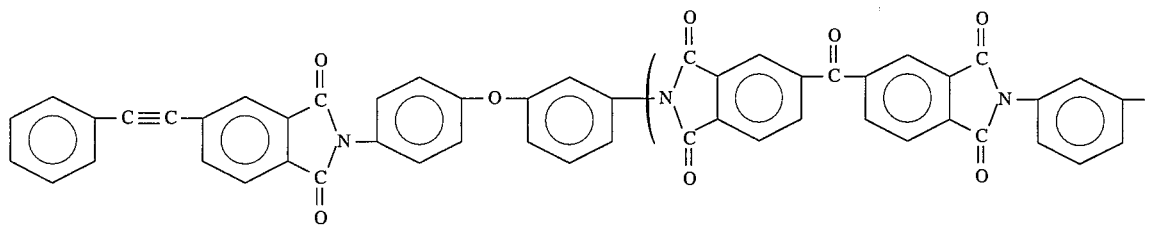

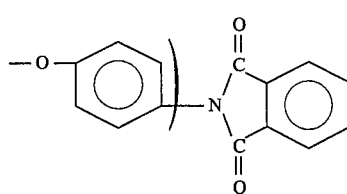
-continued
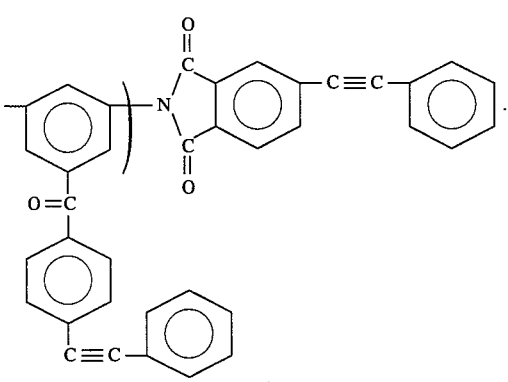

Into a flame dried 100 mL three necked round bottom flask equipped with nitrogen inlet, mechanical stirrer, and drying tube were placed 3,4'-oxydianiline (3.9229 g, 0.0196 mol), 3,5-diamino-4'-phenylethynylbenzophenone (0.6800 g, 0.0022 mol) and 10 mL (30.8% w/w) N-methyl-2-pyrrolidinone (NMP). After dissolution, a slurry of 3,3',4,4'-benzophenonetetracarboxylic dianhydride (6.3494 g, 0.0197 mol) and 4-phenylethynylphthalic anhydride (1.0245 g, 0.0041 mol) in 8 mL (47.2% w/w) of NMP was added and washed in with an additional 9 mL of NMP to afford a 30.0% (w/w) solution. The reaction was stirred at room temperature for 24 h under nitrogen. The inherent viscosity of the amide acid oligomeric solution (0.5% in NMP at 25° C.) was 0.28 dL/g. Approximately 10.5 g of amide acid oligomeric solution was used to cast an unoriented thin film. Toluene (60 mL) was added to the remaining amide acid oligomeric solution and the temperature increased and maintained at ~180° C. for ~16 h under a nitrogen atmosphere. As cyclodehydration to the imide occurred, a precipitate formed. The mixture was cooled, the oligomer was washed in hot water, warm methanol, and dried under vacuum at 220° C. for 1.5 h to provide a tan powder (7.43 g, 66% yield). The $T_g$ of the uncured as-isolated oligomer (DSC, 20° C./min) was 269° C. and the exothermic onset and peak occurred at 352° C. and 399° C., respectively. The $T_g$ of the cured polymer (cure conditions: 350° C./1 h/sealed pan) was 296° C. An unoriented thin films cast from a NMP solution of the amide acid oligomer cured at 100°, 225°, and 350° C. for 1 h each in flowing air was brittle and broke on the plate. The $T_g$ of the cured film was 296° C. Polymer characterization is presented in Table 1.

EXAMPLE 11

0.90:0.10 3,4'-Oxydianiline and 3,5-Diamino-4'-phenylethynylbenzophenone, and Pyromellitic Dianhydride, Using 7.57 mole % Stoichiometric offset and 15.14 mole % 4-Phenylethynylphthalic Anhydride (Calculated $(\overline{M})_n$=5000 g/mole)

The following example illustrates the reaction sequence in FIG. 2 for the preparation of the controlled molecular weight PEPI where Ar' is 3,4'-diphenylether and R is a 4-benzoyl group and Ar is 1,2,4,5-tetrasubstituted benzene, and W is a phenylethynyl group located in the 4 position. The ratio of diamines [Ar':R] is 0.90:0.10. The stoichiometric imbalance is 9.48 mole % and the endcapping reagent is 18.96 mole % of 4-phenylethynylphthalic anhydride.

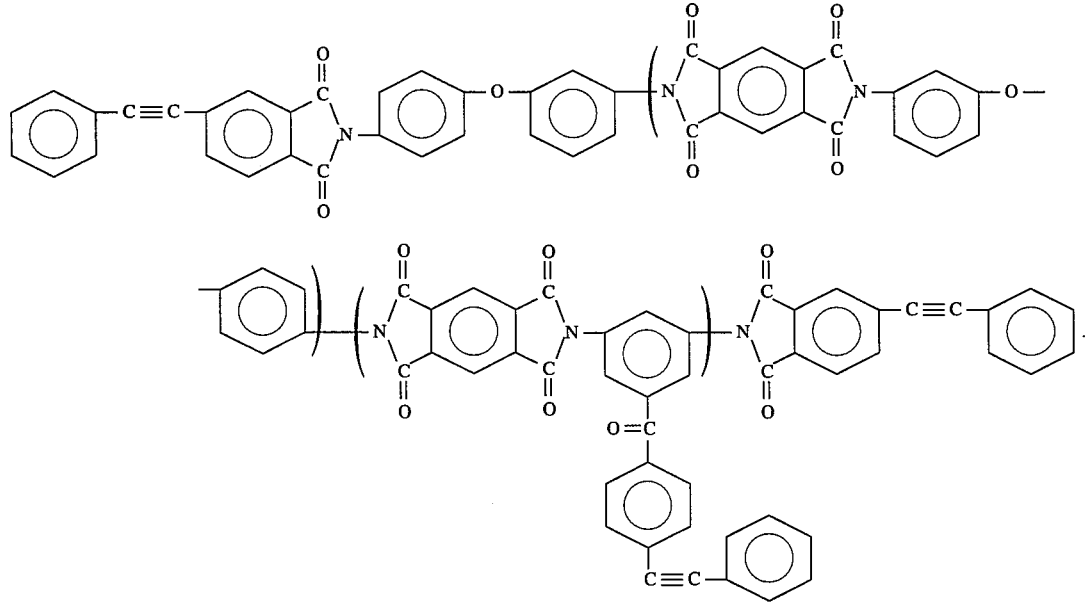

Into a flame dried 100 mL three necked round bottom flask equipped with nitrogen inlet, mechanical stirrer, and drying tube were placed 3,4'-oxydianiline (3.7846 g, 0.0189 mol), 3,5-diamino-4'-phenylethynylbenzophenone (0.6560 g, 0.0021 mol) and 11.0 mL N-methyl-2-pyrrolidinone (NMP). After dissolution, pyromellitic dianhydride, (4.2337 g, 0.01941 mol), and 4-phenylethynylphthalic anhydride (0.7893 g, 0.00318 mol). NMP (10.0 mL) was used to wash in the solid to afford a 30.0% (w/w) solution. The reaction was stirred at room temperature for 24 h under nitrogen. The inherent viscosity of the amide acid oligomeric solution (0.5% in NMP at 25° C.) was 0.36 dL/g. Approximately 7.9 g of amide acid oligomeric solution was used to cast an unoriented thin film. The reaction vessel was fitted with a moisture trap and toluene (40 mL) was added to the remaining amide acid oligomeric solution and the temperature increased and maintained at ~180° C. for ~16 h under a nitrogen atmosphere. As cyclodehydration to the imide occurred, the oligomer began to precipitate. The oligomer was washed in hot water, warm methanol, and dried under vacuum at 230° C. for 4 h to provide a brown powder (6.3 g, 76% yield). The $T_g$ of the uncured as-isolated oligomer (DSC, 20° C./min) was not detected by DSC and the exothermic onset and peak occurred at 340° C. and 423° C., respectively. The $T_g$ of the cured polymer (cure conditions: 350° C./1 h/sealed pan) was not detectable by DSC. Unoriented thin films cast from a NMP solution of the amide acid oligomer cured at 100°, 225°, and 350° C. for 1 h each in flowing air were brittle and cracked up into tiny pieces. The $T_g$ of the cured film was not detectable by DSC. Polymer characterization is presented in Table 1.

EXAMPLE 12

0.90:0.10 3,4'-Oxydianiline and 3,5-Diamino-4'-phenylethynylbenzophenone, and 4,4'-Oxydiphthalic Dianhydride, Using 9.3 mole % Stoichiometric offset and 18.6 mole % 4-Phenylethynylphthalic Anhydride (Calculated $(\overline{M})_n$=5000 g/mole)

The following example illustrates the reaction sequence in FIG. 2 for the preparation of the controlled molecular weight PEPI where Ar' is 3,4'-diphenylether and R is a 4-benzoyl group and Ar is 3,3',4,4'-diphenylether and W is a phenylethynyl group located in the 4 position. The ratio of diamines [Ar':R] is 0.90:0.10. The stoichiometric imbalance is 9.3 mole % and the endcapping reagent is 18.6 mole % of 4-phenylethynylphthalic anhydride.

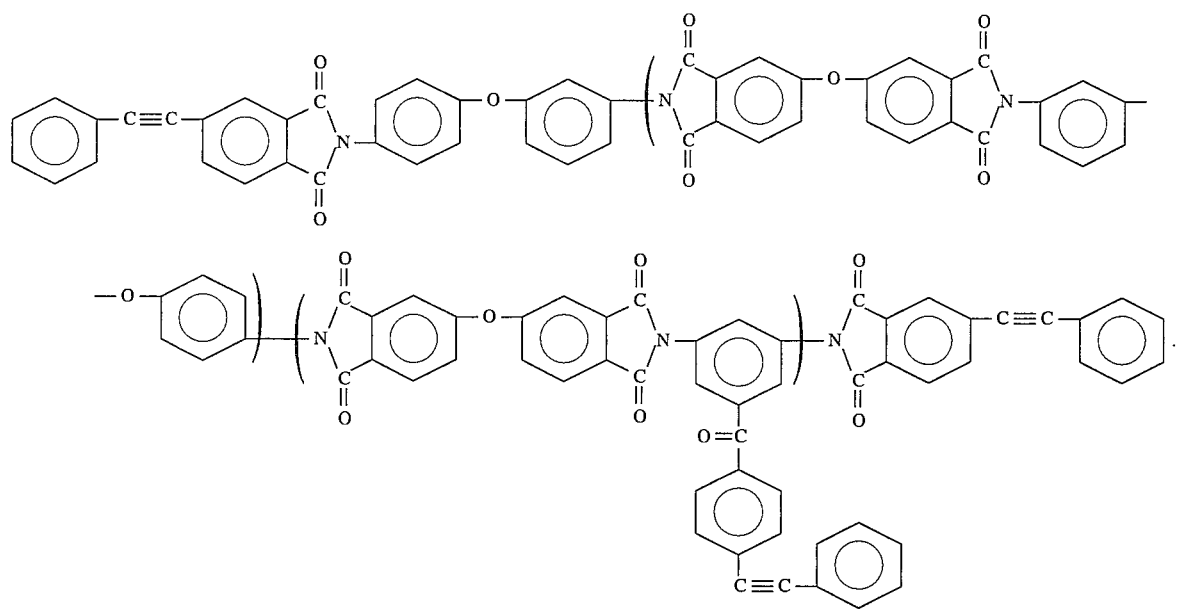

Into a flame dried 100 mL three necked round bottom flask equipped with nitrogen inlet, mechanical stirrer, and drying tube were placed 3,4'-oxydianiline (3.2439 g, 0.0162 mol), 3,5-diamino-4'-phenylethynylbenzophenone (0.5623 g, 0.0018 mol) and 12.0 mL N-methyl-2-pyrrolidinone (NMP). After dissolution, 4,4'-oxydiphthalic dianhydride, (5.0645 g, 0.0163 mol), and 4-phenylethynylphthalic anhydride (0.8311 g, 0.00334 mol). NMP (10.0 mL) was used to wash in the solid to afford a 30.0% (w/w) solution. The reaction was stirred at room temperature for 24 h under nitrogen. The inherent viscosity of the amide acid oligomeric solution (0.5% in NMP at 25° C.) was 0.30 dL/g. Approximately 6.4 g of amide acid oligomeric solution was used to cast an unoriented thin film. The reaction vessel was fitted with a moisture trap and toluene (40 mL) was added to the remaining amide acid oligomeric solution and the temperature increased and maintained at ~180° C. for ~16 h under a nitrogen atmosphere. As cyclodehydration to the imide occurred, the oligomer began to precipitate. The oligomer was washed in hot water, warm methanol, and dried under vacuum at 230° C. for 4 h to provide a brown powder (6.6 g, 75% yield). The $T_g$ of the uncured as-isolated oligomer (DSC, 20° C./min) was ~240° C. by DSC and the exothermic onset and peak occurred at 340° C. and 423° C., respectively. The $T_g$ of the cured polymer (cure conditions:

350° C./1 h/sealed pan) was 260° C. by DSC. Polymer characterization is presented in Table 1.

EXAMPLE 13

0.70:0.15:0.15 3,4'-Oxydianiline,
1,3-bis(3-aminophenoxy)benzene and
3,5'-Diamino-4'-phenylethynylbenzophenone,
3,3',4,4'-Biphenyltetracarboxylic Dianhydride,
Using 9.33 mole % Stoichiometric offset and 18.66 mole % 4-Phenylethynylphthalic Anhydride
(Calculated $(\overline{M})_n = 5000$ g/mole)

The following example illustrates the reaction sequence in FIG. 2 for the preparation of the controlled molecular weight PEPI where Ar'(1) is 3,4'-diphenylether and Ar'(2) is 1,3-diphenoxyphenyl and R is a 4-benzoyl group and Ar is 3,3',4,4'-biphenyl and W is a phenylethynyl group located in the 4 position. The ratio of diamines [Ar' (1):Ar' (2):R] is 0.70:0.15:0.15. The stoichiometric imbalance is 9.33 mole % and the endcapping reagent is 18.66 mole % of 4phenylethynylphthalic anhydride.

Into a flame dried 100 mL three necked round bottom flask equipped with nitrogen inlet, mechanical stirrer, and drying tube were placed 3,4'-oxydianiline (3.3565 g, 0.0168 mol), 1,3-bis(3-aminophenoxy)benzene (1.0501 g, 0.0036 mol), 3,5-diamino-4'-phenylethynylbenzophenone (1.1220 g, 0.0036 mol) and 10 mL of N-methyl-2-pyrrolidinone (NMP). After dissolution, a slurry of 3,3',4,4'-biphenyltetracarboxylic dianhydride (6.3881 g, 0.0217 mol) and 4-phenylethynyl phthalic anhydride.(1.1092 g, 0.0045 mol) in 9 mL (22.6% w/w) of NMP was added and washed in with an additional 10 mL of NMP to afford a 30.28% (w/w) solution. The reaction was stirred at room temperature for 24 h under nitrogen. The inherent viscosity of the amide acid oligomeric solution (0.5% in NMP at 25° C.) was 0.29 dL/g. Approximately 12.6 g of amide acid oligomeric solution was used to cast an unoriented thin film. Toluene (60 mL) was added to the remaining amide acid oligomeric solution and the temperature increased and maintained at ~180° C. for ~16 h under a nitrogen atmosphere. As cyclodehydration to the imide occurred, the oligomer precipitated in solution. The oligomer was washed in hot water, warm methanol, and dried under vacuum at 230° C. for 2 h to provide a brown powder (8.07 g, 66% yield). The inherent viscosity of the imide oligomer (0.5% in m-cresol at 25° C.) was 0.32 dL/g. The $T_g$ of the uncured as-isolated oligomer (DSC, 20° C./min) was 224° C. with a $T_m$ at 284° C. and the exothermic onset and peak occurred at 363° C. and 416° C., respectively. The $T_g$ of the cured polymer (cure conditions: 350° C./1 h/sealed pan) was 289° C. Unoriented thin films cast from a NMP solution of the amide acid oligomer cured at 100°, 225°, and 350° C. for 1 h each in flowing air gave tensile strength, tensile modulus, and elongation at 23° C. of 20.4 ksi, 492 ksi, and 15%; at 177° C. of 11.2 ksi, 307 ksi, and 24% and at 200° C. of 9.9 ksi, 285 ksi, and 28%, respec-

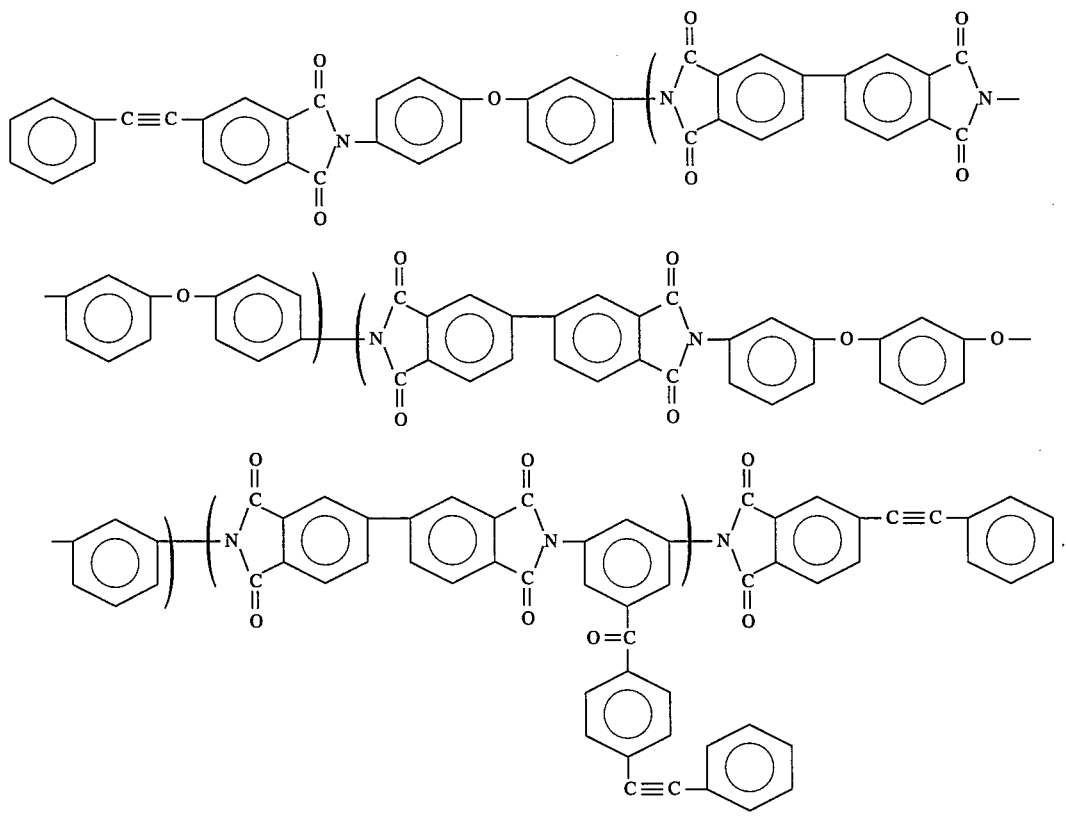

tively. The $T_g$ of the cured film was 301° C. A sample compression molded at 371° C./200 psi/1 h had a $G_{IC}$ (critical strain energy release rate) of 6.2 in lb/in². Polymer characterization is presented in Table 1, thin film mechanical properties are presented in Table 2 and adhesive properties are presented in Table 3.

Mixtures of dianhydrides were used to alter properties as illustrated in Examples 14 and 15.

EXAMPLE 14

0.90:0.10 3,4'-Oxydianiline and
3,5-Diamino-4'-phenylethynylbenzophenone, and
0.85:0.15 3,3',4,4'-Benzophenonetetracarboxylic
Dianhydride and 4,4'-Oxydiphthalic Anhydride,
Using 9.02 mole % Stoichiometric offset and 18.04
mole % 4-Phenylethynylphthalic Anhydride
(Calculated $(\overline{M})_n$=5000 g/mole)

The following example illustrates the reaction sequence in FIG. 2 for the preparation of the controlled molecular weight PEPI where Ar' is 3,4'-diphenylether and R is a 4-benzoyl group; Ar (1) is 3,3',4,4'-diphenylether and Ar (2) is 3,3',4,4'-benzophenone and W is a phenylethynyl group located in the 4 position. The ratio of diamines [Ar' (1):Ar' (2)] is 0.90:0.10 and the ratio of dianhydrides [Ar (1):Ar (2)] is 0.15:0.85. The stoichiometric imbalance is 9.02 mole % and the endcapping reagent is 18.04 mole % of 4-phenylethynylphthalic anhydride

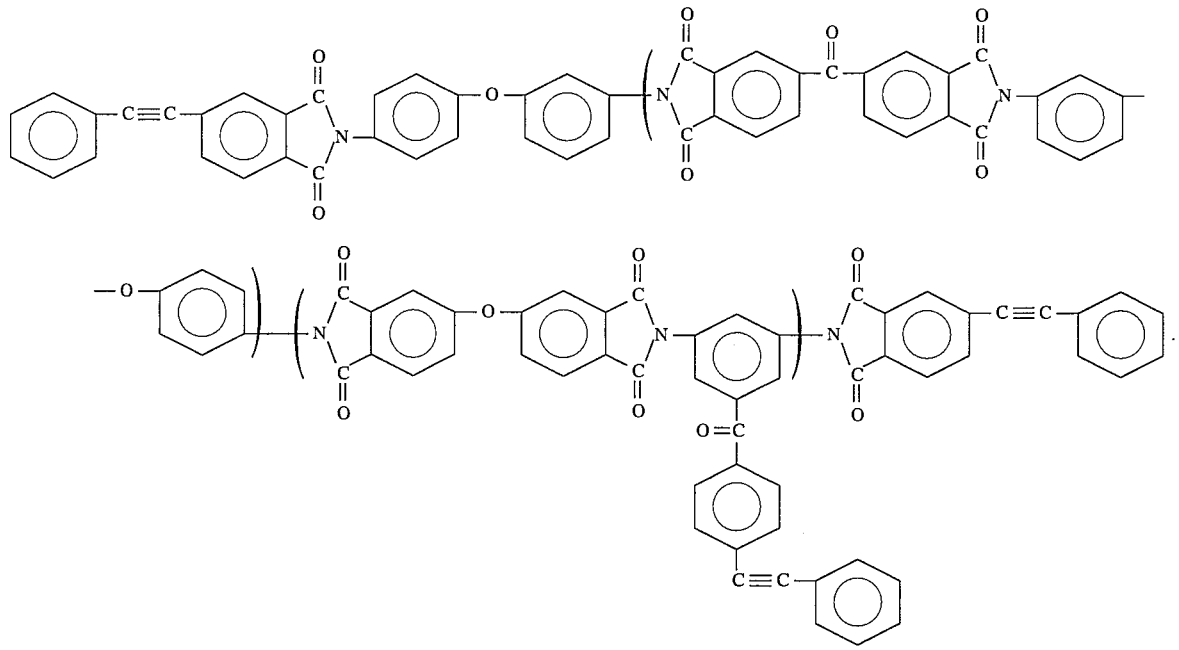

Into a flame dried 100 mL three necked round bottom flask equipped with nitrogen inlet, mechanical stirrer, and drying tube were placed 3,4'-oxydianiline (4.6046 g, 0.0230 mol), 3,5-diamino-4'-phenylethynylbenzophenone (0.7981 g, 0.0026 mol) and 9 mL (36.8% w/w) N-methyl-2-pyrrolidinone (NMP). After dissolution, a slurry of 3,3',4,4'-biphenyltetracarboxylic dianhydride (5.8134 g, 0.0198 mol), 4,4'-oxydiphthalic anhydride (1.0817 g, 0.0035 mol) and 4-phenylethynylphthalic anhydride (1.1436 g, 0.0046 mol) in 10 mL (43.4% w/w) of NMP was added and washed in with an additional 11 mL of NMP to afford a 30.3% (w/w) solution. The reaction was stirred at room temperature for 24 h under nitrogen. The inherent viscosity of the amide acid oligomeric solution (0.5% in NMP at 25° C.) was 0.35 dL/g. Approximately 10.6 g of amide acid oligomeric solution was used to cast an unoriented thin film. Toluene (60 mL) was added to the remaining amide acid oligomeric solution and the temperature increased and maintained at ~180° C. for ~16 h under a nitrogen atmosphere. As cyclodehydration to the imide occurred, the oligomer remained in solution. As the mixture was cooled, a precipitate formed. The oligomer was washed in hot water, warm methanol, and dried under vacuum at 220° C. for 1.5 h to provide a brown powder (9.47 g, 76% yield). The inherent viscosity of the imide oligomer (0.5% in m-cresol at 25° C.) was 0.26 dL/g. The $T_g$ of the uncured as-isolated oligomer (DSC, 20° C./min) was not detected with $T_m$ at 243° and 262° C. and the exothermic onset and peak occurred at 320° C. and 391° C., respectively. The $T_g$ of the cured polymer (cure conditions: 350° C./1 h/sealed pan) was 310° C. Unoriented thin films cast from a NMP solution of the amide acid oligomer cured at 100°, 225°, and 350° C. for 1 h each in flowing air gave tensile strength, tensile modulus, and elongation at 23° C. of 19.8 ksi, 489 ksi, and 12%; at 177° C. of 10.7 ksi, 290 ksi, and 11% and at 200° C. of 10.3 ksi, 329 ksi, and 11%, respectively. The $T_g$ of the cured film was 294° C. Polymer characterization is presented in Table 1 and thin film mechanical properties are presented in Table 2.

EXAMPLE 15

0.90:0.10 3,4'-Oxydianiline and
3,5-Diamino-4'-phenylethynylbenzophenone,
0.70:0.30 3,3',4,4'-Benzophenonetetracarboxylic
Dianhydride and 4,4'-Oxydiphthalic Anhydride,
Using 9.06 mole % Stoichiometric offset and 18.12
mole % 4-Phenylethynylphthalic Anhydride
(Calculated $(\overline{M})_n$=5000 g/mole)

The following example illustrates the reaction sequence in FIG. 2 for the preparation of the controlled molecular weight PEPI where Ar' is 3,4'-diphenylether and R is a 4-benzoyl group; Ar (1) is 3,3',4,4'-diphenylether and Ar (2) is 3,3',4,4'-biphenyl and W is a phenylethynyl group located in the 4 position. The ratio of diamines [Ar' (1):Ar' (2)] is 0.90:0.10 and the ratio of dianhydrides [Ar (1):Ar (2)] is 0.30:0.70. The stoichiometric imbalance is 9.06 mole % and the endcapping reagent is 18.12 mole % of 4-phenylethynylphthalic anhydride

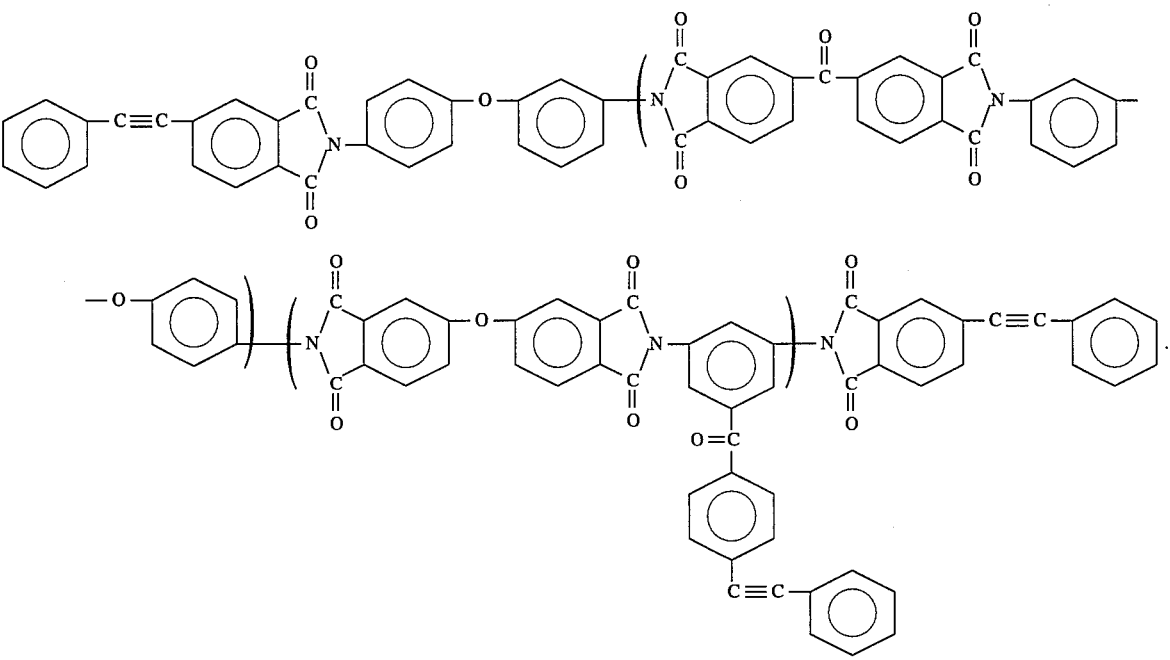

Into a flame dried 100 mL three necked round bottom flask equipped with nitrogen inlet, mechanical stirrer, and drying tube were placed 3,4'-oxydianiline (4.6301 g, 0.0231 mol), 3,5-diamino-4'-phenylethynylbenzophenone (0.8025 g, 0.0026 mol) and 10 mL (34.5% w/w) N-methyl-2-pyrrolidinone (NMP). After dissolution, a slurry of 3,3',4,4'-biphenyltetracarboxylic dianhydride (4.8118 g, 0.0164 mol), 4,4'-oxydiphthalic anhydride (2.1744 g, 0.0070 mol) and 4phenylethynylphthalic anhydride ( 1.1556 g, 0.0047 mol) in 10 mL (44.1% w/w) of NMP was added and washed in with an additional 10 mL of NMP to afford a 30.5% (w/w) solution. The reaction was stirred at room temperature for 24 h under nitrogen. The inherent viscosity of the amide acid oligomeric solution (0.5% in NMP at 25° C.) was 0.33 dL/g. Approximately 10.9 g of amide acid oligomeric solution was used to cast an unoriented thin film. Toluene (60 mL) was added to the remaining amide acid oligomeric solution and the temperature increased and maintained at ~180° C. for ~16 h under a nitrogen atmosphere. As cyclodehydration to the imide occurred, the oligomer remained in solution. As the mixture was cooled, a precipitate formed. The oligomer was washed in hot water, warm methanol, and dried under vacuum at 230° C. for 4 h to provide a brown powder (7.98 g, 63% yield). The inherent viscosity of the imide oligomer (0.5% in m-cresol at 25° C.) was 0.31 dL/g. The $T_g$ of the uncured as-isolated oligomer (DSC, 20° C./min) was 227° C. with a $T_m$ at 260° C. and the exothermic onset and peak occurred at 340° C. and 419° C., respectively. The $T_g$ of the cured polymer (cure conditions: 350° C./1 h/sealed pan) was 299° C. Unoriented thin films cast from a NMP solution of the amide acid oligomer cured at 100°, 225°, and 350° C. for 1 h each in flowing air gave tensile strength, tensile modulus, and elongation at 23° C. of 19.5 ksi, 457 ksi, and 16%; at 177° C. of 10.1 ksi, 291 ksi, and 20% and at 200° C. of 9.2 ksi, 299 ksi, and 12%, respectively. The $T_g$ of the cured film was 296° C. Polymer characterization is presented in Table 1 and thin film mechanical properties are presented in Table 2.

EXAMPLE 16

3,5-Diamino-4'-phenylethynylbenzophenone and 3,3',4,4'-Biphenyltetracarboxylic Dianhydride, Using 10.80 mole % Stoichiometric offset and 21.60 mole % 3-Aminophenoxy-4'-phenylethynylbenzophenone (Calculated $(\overline{M})_n$=5000 g/mole)

The following example illustrates the reaction sequence in FIG. 5 for the preparation of the controlled molecular weight PEPI where Ar is 1,3-diphenylene, R is a 4-benzoyl group and Ar is 3,3',4,4'-biphenyl and Z is a phenoxy-4'-phenylethynylbenzophenone group located in the 3 position. The stoichiometric imbalance is 10.80 mole % and the endcapping reagent is 21.60 mole % of 3-aminophenoxy-4'-phenylethynylbenzophenone.

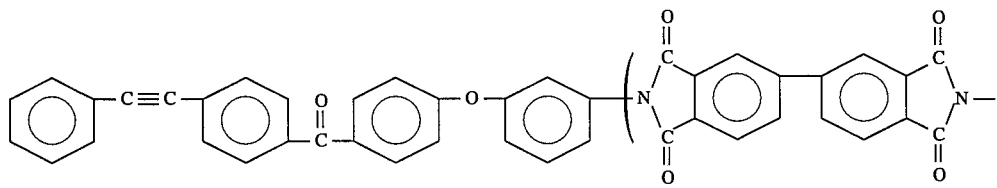

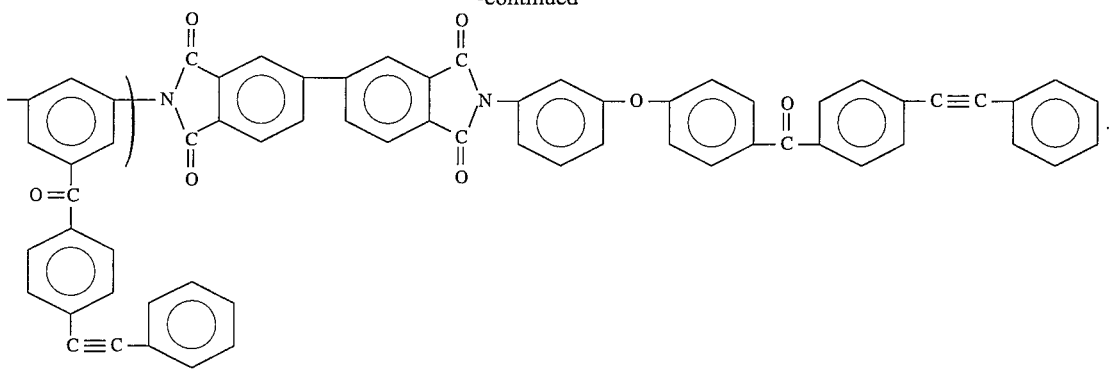

Into a flame dried 100 mL three necked round bottom flask equipped with nitrogen inlet, mechanical stirrer, and drying tube were placed 3,5-diamino-4'-phenylethynylbenzophenone (2.5741 g, 0.0082 mol) and 3-aminophenoxy-4'-phenylethynylbenzophenone (0.7771 g, 0.0020 mol) and 6 mL (35.1% w/w) N-methyl-2-pyrrolidinone (NMP). After dissolution, a slurry of 3,3',4,4'-biphenyltetracarboxylic dianhydride (2.7181 g, 0.0092 mol) in 3 mL (46.7% w/w) of NMP was added and washed in with an additional 5 mL of NMP to afford a 29.6% (w/w) solution. The reaction was stirred at room temperature for 24 h under nitrogen. The inherent viscosity of the amide acid oligomeric solution (0.5% in NMP at 25° C.) was 0.22 dL/g. Approximately 10.84 g of amide acid oligomeric solution was used to cast an unoriented thin film. Toluene (60 mL) was added to the remaining amide acid oligomeric solution and the temperature increased and maintained at ⁻180° C. for ⁻16 h under a nitrogen atmosphere. As cyclodehydration to the imide occurred, a precipitate formed. The mixture was cooled, the Toluene (60 mL) was added to the remaining amide acid oligomeric solution and the temperature increased and maintained at ⁻180° C. for ⁻16 h under a nitrogen atmosphere. As cyclodehydration to the imide occurred, a precipitate formed. The mixture was cooled, the oligomer was washed in hot water, warm methanol, and dried under vacuum at 230° C. for 4 h to provide a tan powder (2.27 g, 40% yield). The $T_g$ of the uncured as-isolated oligomer (DSC, 20° C./min) was not detected by DSC and the exothermic onset and peak was washed in hot water, warm methanol, and dried under vacuum at 230° C. for 4 h to provide a tan powder (2.27 g, 40% yield). The $T_g$ of the uncured as-isolated oligomer (DSC, 20° C./min) was not detected by DSC and the exothermic onset and peak occurred at 290° C. and 368° C., respectively. The $T_O$ Of the cured polymer (cure conditions: 350° C./1 h/sealed pan) was not detected by DSC. The unoriented thin films cast from a NMP solution of the amide acid oligomer cured at 100°, 225°, and 350° C. for 1 h each in flowing air was brittle. The $T_g$ of the cured film was not detected by DSC. Polymer characterization is presented in Table 1.

EXAMPLE 17

3,5-Diamino-4'-phenylethynylbenzophenone and 3,3',4,4'-Biphenyltetracarboxylic Dianhydride, Using 10.80 mole % Stoichiometric offset and 21.60 mole % 4-Phenylethynylphthalic Anhydride (Calculated $(\overline{M})_n$=5000 g/mole)

The following example illustrates the reaction sequence in equation 4 for the preparation of the controlled molecular weight PEPI where R is a 4-benzoyl group and Ar is 3,3',4,4'-biphenyl and W is a phenylethynyl group located in the 4 position. The stoichiometric imbalance is 10.80 mole % and the endcapping reagent is 21.60 mole % of 4-phenylethynylphthalic anhydride.

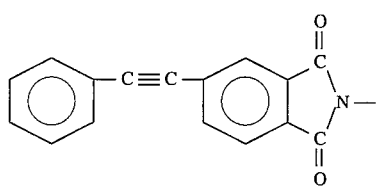

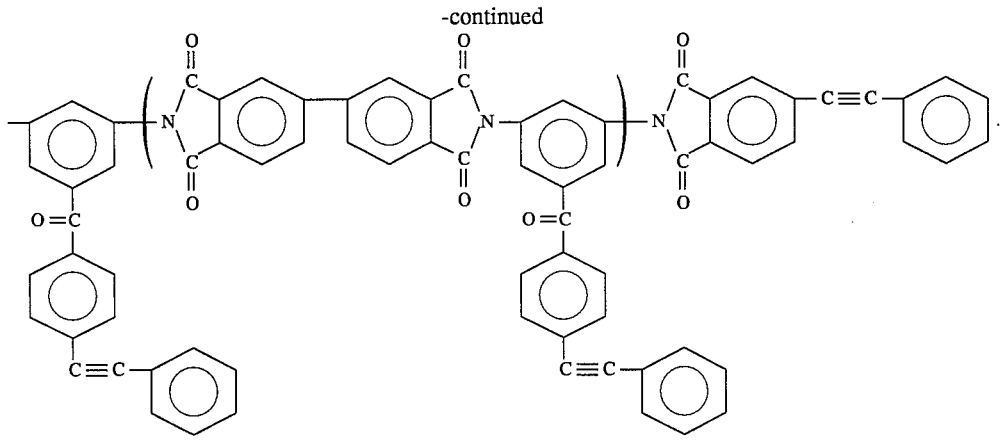
-continued

Into a flame dried 100 mL three necked round bottom flask equipped with nitrogen inlet, mechanical stirrer, and drying tube were placed 3,5-diamino-4'-phenylethynylbenzophenone (2.8499 g, 0.0091 mol) and 4 mL (40.8% w/w) of N-methyl-2-pyrrolidinone (NMP). After dissolution, a slurry of 3,3',4,4'-biphenyltetracarboxylic dianhydride (2.3944 g, 0.0081 mol) and 4-phenylethynylphthalic anhydride (0.4892 g, 0.0020 mol) in 4 mL (41.1% w/w) of NMP was added and washed in with an additional 5 mL of NMP to afford a 29.9% (w/w) solution. The reaction was stirred at room temperature for 24 h under nitrogen. The inherent viscosity of the amide acid oligomeric solution (0.5% in NMP at 25° C.) was 0.21 dL/g. Approximately 9.95 g of amide acid oligomeric solution was used to cast an unoriented thin film. Toluene (60 mL) was added to the remaining amide acid oligomeric solution and the temperature increased and maintained at ~180° C. for ~16 h under a nitrogen atmosphere. As cyclodehydration to the imide occurred, a precipitate formed. The mixture was cooled, the oligomer was washed in hot water, warm methanol, and dried under vacuum at 230° C. for 4 h to provide a brown powder (1.75 g, 32% yield). The $T_0$ of the uncured as-isolated oligomer (DSC, 20° C./min) Was not detected by DSC and the exothermic onset and peak occurred at 299° C. and 376° C., respectively. The $T_g$ of the cured polymer (cure conditions: 350° C./1 h/sealed pan) was not detected by DSC. The unoriented thin films cast from a NMP solution of the amide acid oligomer cured at 100°, 225°, and 350° C. for 1 h each in flowing air was brittle. The $T_g$ of the cured film was not detected by DSC. Polymer characterization is presented in Table 1.

Oligomer and polymer characterization is presented in Table 1, unoriented thin film properties are presented in Table 2, preliminary titanium (Ti) to Ti tensile shear adhesive properties are presented in Table 3, and preliminary composite properties are presented in Table 4.

What is claimed is:

1. Controlled molecular weight copolyimides containing pendent phenylethynyl groups and chain terminated with either nonreactive or reactive phthalic anhydride based endcapping agents have the following repeat unit:

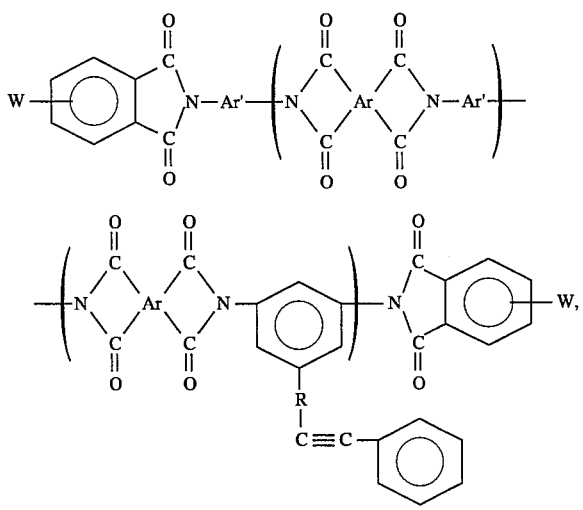

wherein Ar is a member selected from the group consisting of:

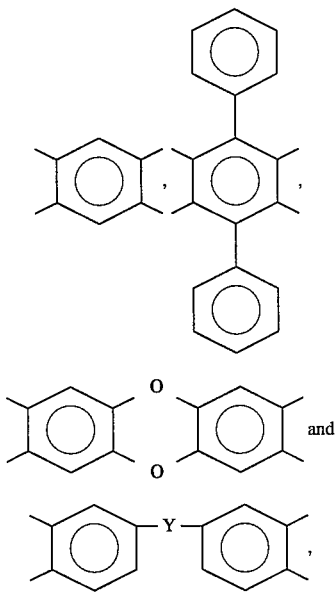

wherein Y is a bond or Y is a radical selected from the group consisting of:

O, CO, SO$_2$, C(CF$_3$)$_2$, isophthalpyl, terephthaloyl, 1,3-diphenoxy and 1,4-diphenoxy, wherein Ar' is a member selected from the group consisting of:

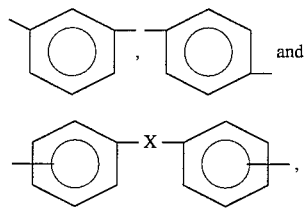
and wherein the catenation is selected from the group consisting of 2,2'; 2,3'; 2,4'; 3,3'; 3,4'; and 4,4' and X is a bond or X is a radical selected from the group consisting of:

CH$_2$, O, CO, CH(OH), C(CF$_3$)$_2$

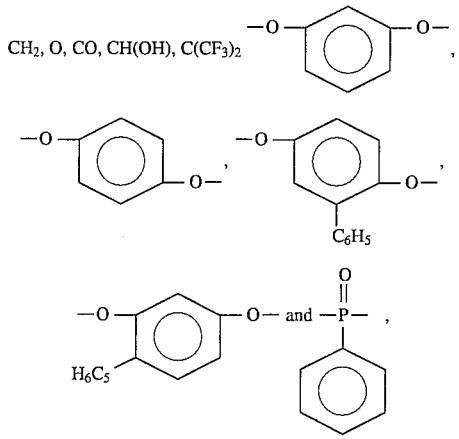

wherein W is a radical selected from the group consisting of: H,

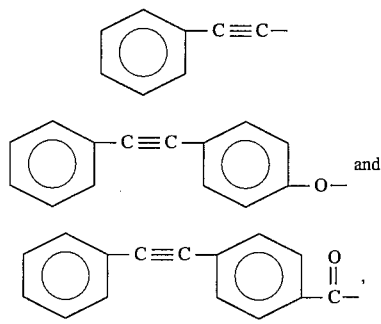

wherein R is a radical selected from the group consisting of:

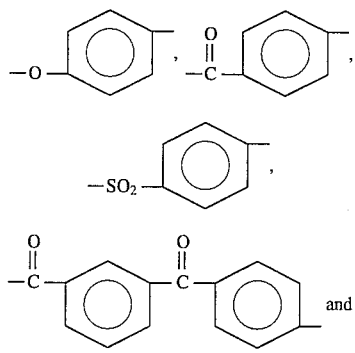

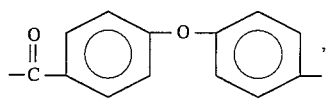

wherein the amount of diamine containing pendent phenylethynyl groups ranges from 1–99 mole %.

2. Controlled molecular weight copolyimides containing pendent phenylethynyl groups and chain terminated with either nonreactive or reactive phthalic anhydride based endcapping agents of claim 1 wherein Ar is a radical selected from the group consisting of:

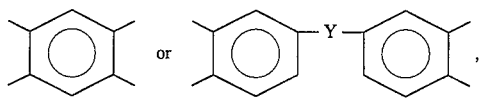

wherein Y is a bond or Y is a radical selected from the group consisting of:

O, and CO, wherein W is a radical selected from the group consisting of: H, and

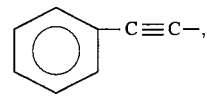

wherein Ar' is a radical selected from the group consisting of:

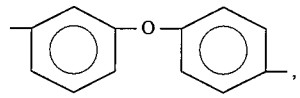

wherein the amount of diamine containing pendent phenylethynyl groups ranges from 10–30 mole %.

3. Controlled molecular weight copolyimides containing pendent phenylethynyl groups of claim 1 wherein Ar is a radical selected from the group consisting of:

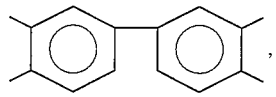

wherein W is a radical selected from the group consisting of:

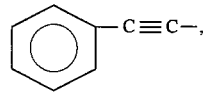

Wherein Ar' is a radical selected from the group consisting of:

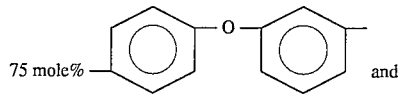

15 mole% 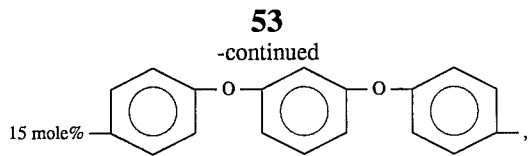

wherein the amount of diamine containing pendent phenylethynyl groups is 10 mole %.

4. Controlled molecular weight copolyimides containing pendent phenylethynyl groups of claim 1 wherein Ar' is

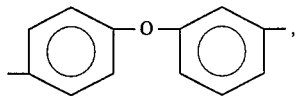

wherein Ar is a radical represented by 50 mole% 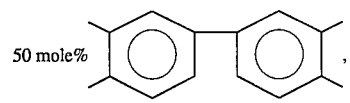

50 mole% 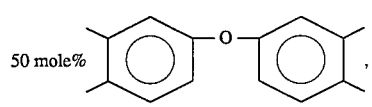

wherein the amount of diamine containing pendent phenylethynyl groups is 10 or 15 mole %.

5. Controlled molecular weight copolyimides containing pendent phenylethynyl groups and chain terminated with either nonreactive or reactive aniline based endcapping agents have the following repeat unit:

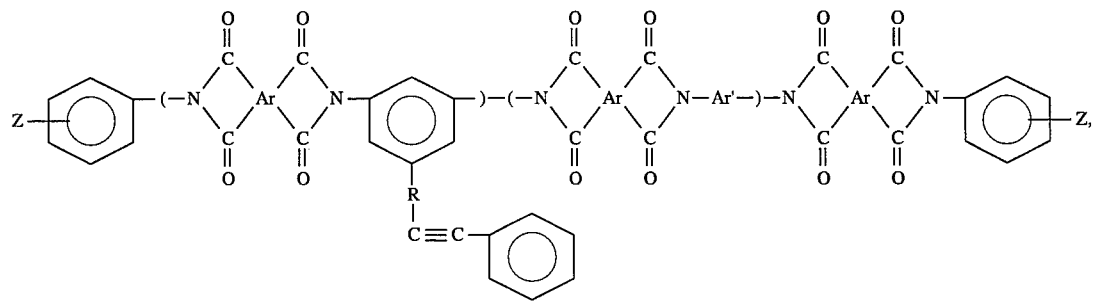

wherein Ar is a member selected from the group consisting of:

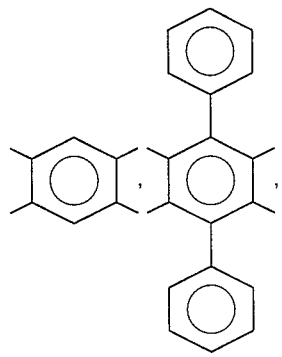

and wherein Y is a bond or Y is a radical selected from the group consisting of:

O, CO, SO$_2$, C(CF$_3$)$_2$, isophthalpyl, terephthaloyl, 1,3-diphenoxy and 1,4-diphenoxy, wherein Ar' is a member selected from the group consisting of:

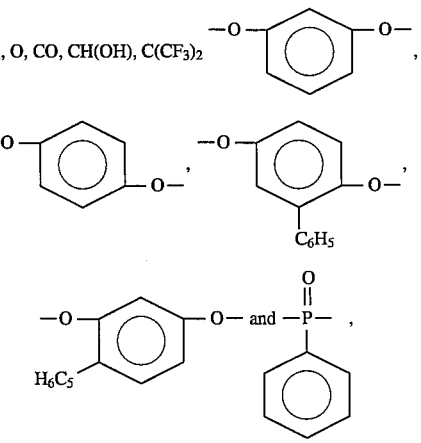

wherein the catenation is selected from the group consisting of 2,2'; 2,3'; 2,4'; 3,3'; 3,4'; and 4,4' and X is a bond or X is a radical selected from the group consisting of:

CH$_2$, O, CO, CH(OH), C(CF$_3$)$_2$ wherein Z is a radical selected from the group consisting of:
H,

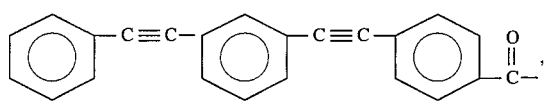

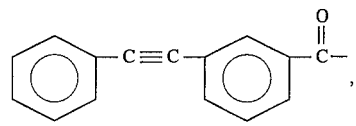

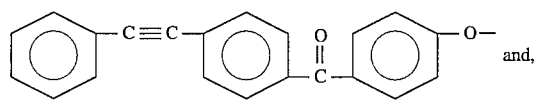 and,

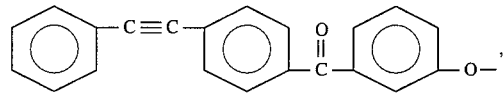

wherein R is a radical selected from the group consisting of:

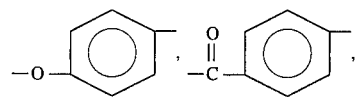

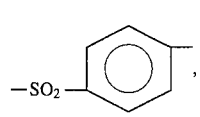

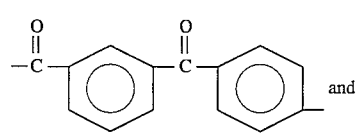 and

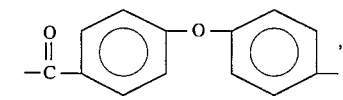

wherein the amount of diamine containing pendent phenylethynyl groups ranges from 1–99 mole %.

6. Controlled molecular weight copolyimides containing pendent phenylethynyl groups of claim 5 wherein Ar is a radical represented by:

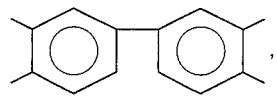

wherein Ar' is a radical represented by:

wherein W is is a radical represented by:

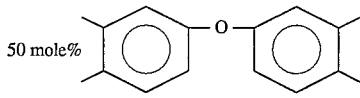

wherein the amount of diamine containing pendent phenylethynyl is 15 mole %.

7. Controlled molecular weight copolyimides containing pendent phenylethynyl groups of claim 5 wherein Ar' is

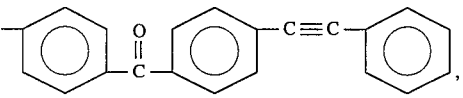

wherein Ar is a radical represented by 50 mole%

50 mole%

Z is a radical represented by:

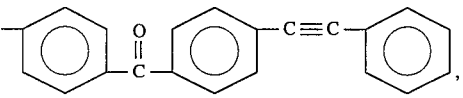

wherein the amount of diamine containing pendent phenylethynyl groups is 10 or 15 mole %.

8. Controlled molecular weight polyimides containing pendent phenylethynyl groups and chain terminated with either nonreactive or reactive phthalic anhydride based endcapping agents have the following repeat unit:

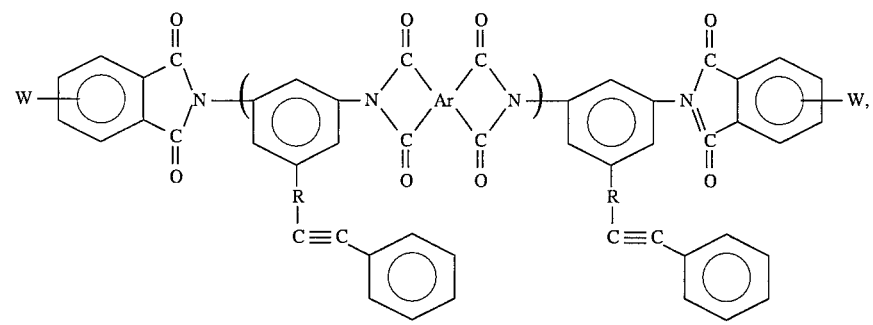

wherein Ar is a member selected from the group consisting of:

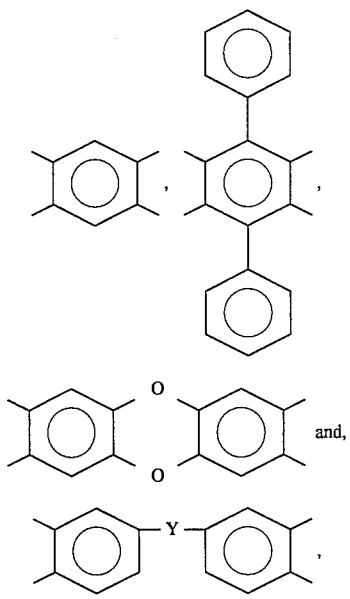

wherein Y is a bond or Y is a radical selected from the group consisting of: O, CO, SO$_2$, C(CF$_3$)$_2$, isophthalpyl, terephthaloyl, 1,3-diphenoxy and 1,4-diphenoxy, wherein W is a radical selected from the group consisting of: H,

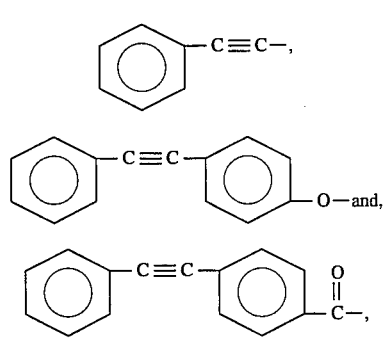

wherein R is a radical selected from the group consisting of:

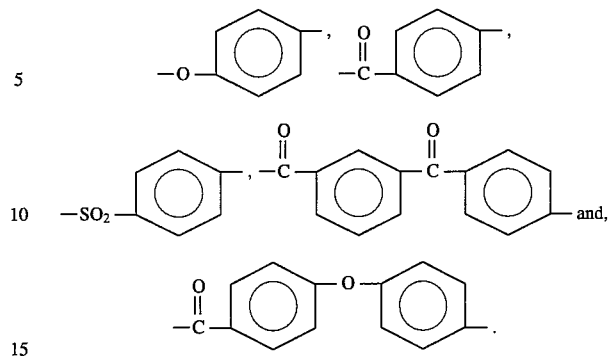

9. Controlled molecular weight polyimides containing pendent phenylethynyl groups and chain terminated with either nonreactive or reactive aniline based endcapping agents have the following repeat unit:

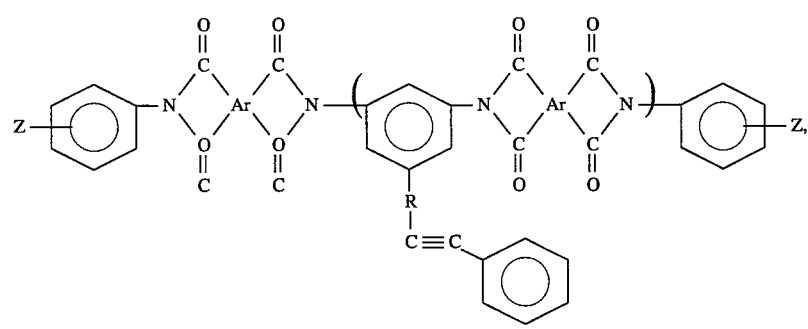

wherein Ar is a member selected from the group consisting of:

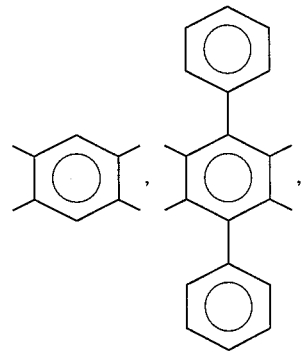

-continued

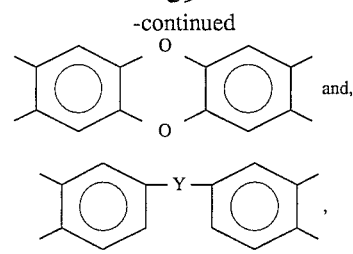

wherein Y is a bond or Y is a radical selected from the group consisting of:
O, CO, SO$_2$, C(CF$_3$)$_2$, isophthalpyl, terephthaloyl, 1,3-diphenoxy and 1,4-diphenoxy, wherein Ar' is a member selected from the group consisting of:

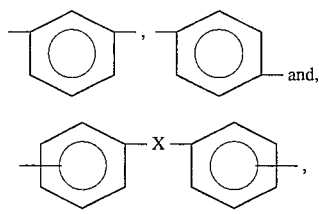

wherein Z is a radical selected from the group consisting of: H,

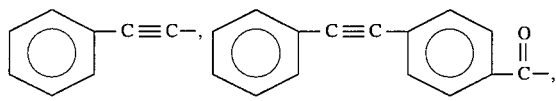

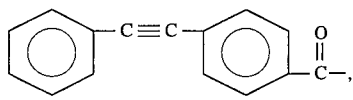

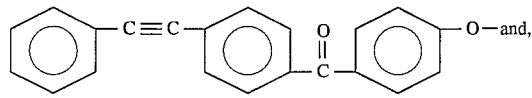

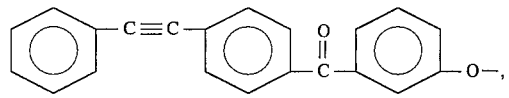

wherein R is a radical selected from the group consisting of:

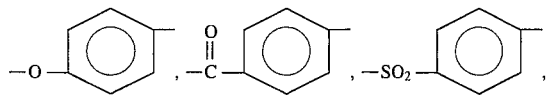

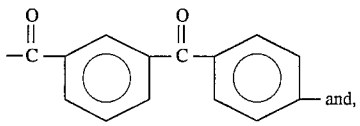

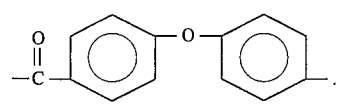

10. Unendcapped polyimides containing pendent phenylethynyl groups having the following general structure:

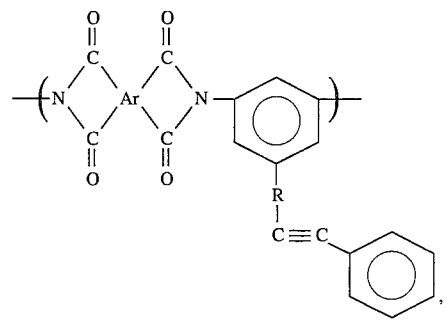

wherein Ar is a member selected from the group consisting of:

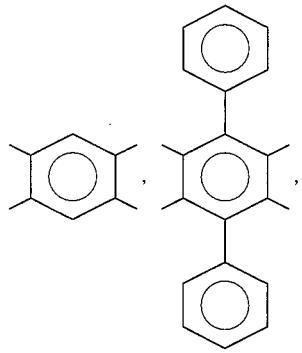

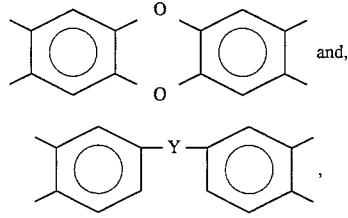

wherein Y is a bond or Y is a radical selected from the group consisting of: O, CO, SO$_2$, C(CF$_3$)$_2$, isophthalpyl, terephthaloyl, 1,3-diphenoxy and 1,4-diphenoxy, wherein R is a radical selected from the group consisting of:

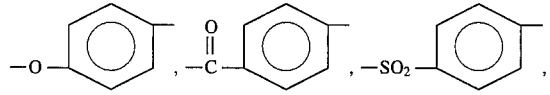

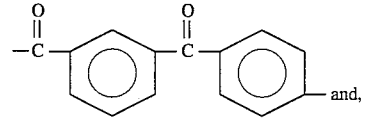

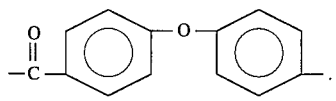

11. The unendcapped polyimide containing pendent phenylethynyl groups of claim 10 wherein Ar is equal to:

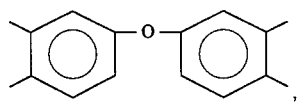

and R is equal to:

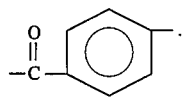

12. Controlled molecular weight amic acid co-oligomers containing pendent phenylethynyl groups and chain terminated with either nonreactive or reactive phthalic anhydride based endcapping agents have the following repeat unit:

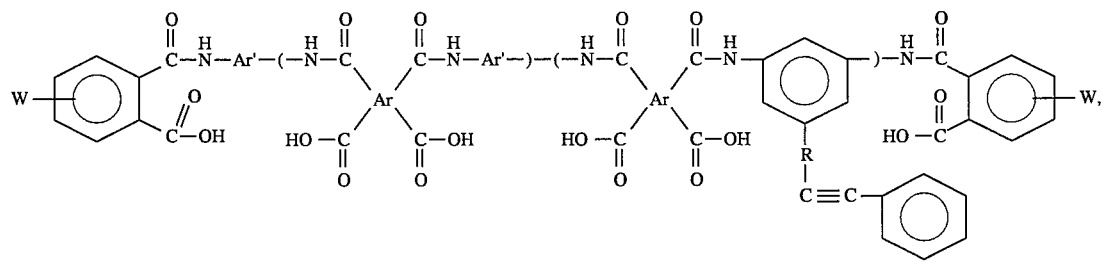

wherein Ar is a member selected from the group consisting of:

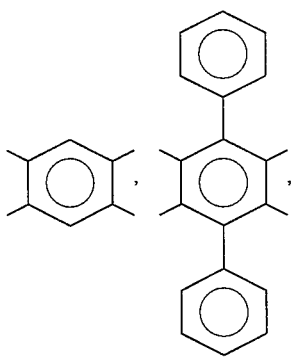

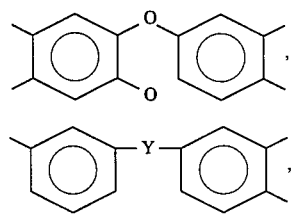

wherein Y is a bond or Y is a radical selected from the group consisting of:

O, CO, $SO_2$, $C(CF_3)_2$, isophthalpyl, terephthaloyl, 1,3-diphenoxy and 1,4-diphenoxy, wherein Ar' is a member selected from the group consisting of:

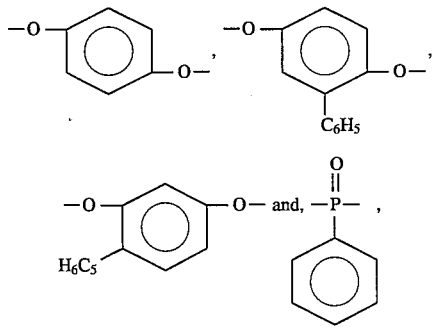

wherein the catenation is selected from the group consisting of 2,2'; 2,3'; 2,4'; 3,3'; 3,4'; and 4,4' and X is a bond or X is a radical selected from the group consisting of:

$CH_2$, O, CO, CH(OH), $C(CF_3)_2$ 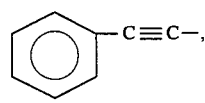

-continued wherein W is a radical selected from the group consisting of:
H, wherein R is a radical selected from the group consisting of:

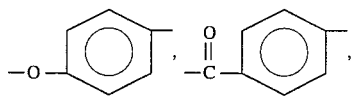

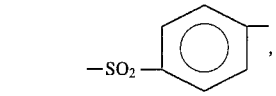

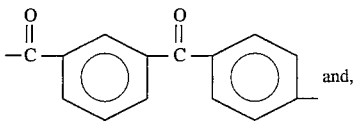 and,

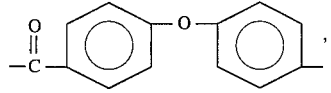

wherein the amount of diamine containing pendent phenylethynyl groups ranges from 1–99 mole %.

13. Controlled molecular weight amic acid co-oligomers containing pendent phenylethynyl groups of claim 12 wherein Ar is a radical selected from the group consisting of:

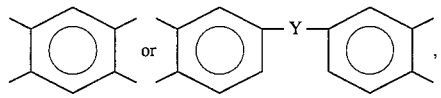

wherein Y is a bond or Y is a radical selected from the group consisting of:

O, and CO, wherein W is a radical selected from the group consisting of: H, and

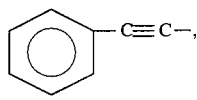

wherein Ar' is a radical selected from the group consisting of:

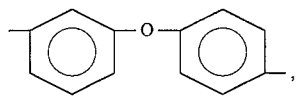

wherein the amount of diamine containing pendent phenylethynyl groups ranges from 10–30 mole %.

14. Controlled molecular weight amic acid co-oligomers containing pendent phenylethynyl groups of claim 12 wherein Ar is radical selected from the group consisting of:

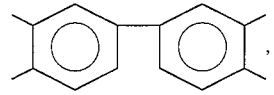

wherein W is a radical selected from the group consisting of:

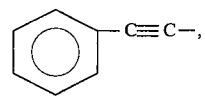

wherein Ar' is a radical selected from the group consisting of:

75 mole % 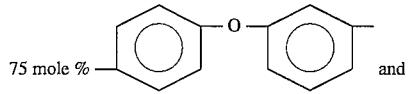 and 15 mole % 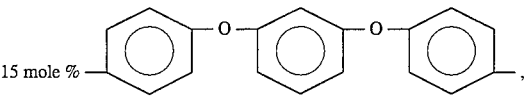, wherein the amount of diamine containing pendent phenylethynyl groups is 10 mole %.

15. Controlled molecular weight amic acid co-oligomers containing pendent phenylethynyl groups of claim 12 wherein Ar' is a radical selected from the group consisting of:

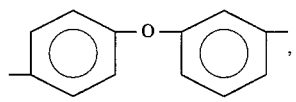

wherein Ar is a radical represented by 50 mole % , 50 mole % 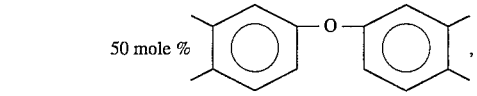, wherein the amount of diamine containing pendent phenylethynyl groups is 10 or 15 mole %.

16. Controlled molecular weight amic acid co-oligomers containing pendent phenylethynyl groups and chain terminated with either nonreactive or reactive aniline based endcapping agents have the following repeat unit:

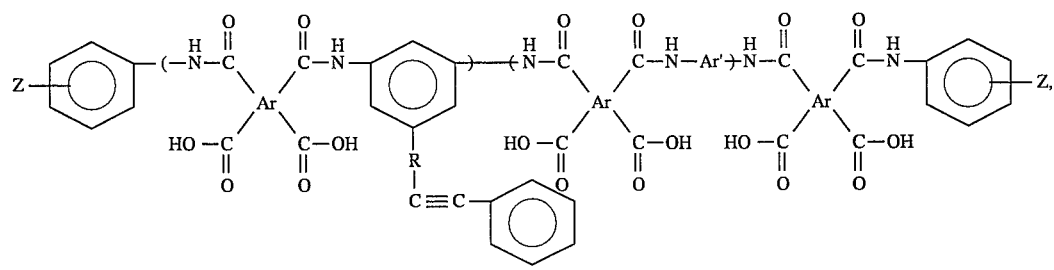

wherein Ar is a member selected from the group consisting of:

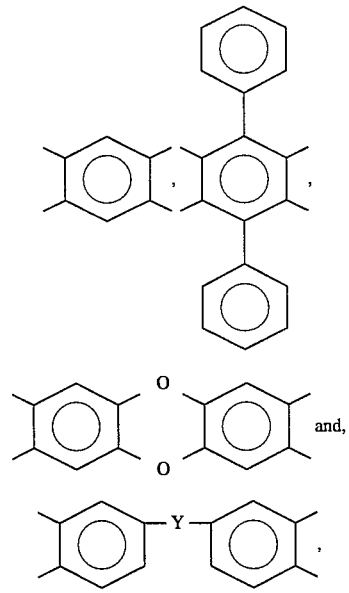

wherein Y is a bond or Y is a radical selected from the group consisting of:

O, CO, SO$_2$, C(CF$_3$)$_2$, isophthalpyl, terephthaloyl, 1,3-diphenoxy and 1,4-diphenoxy, wherein Ar' is a member selected from the group consisting of:

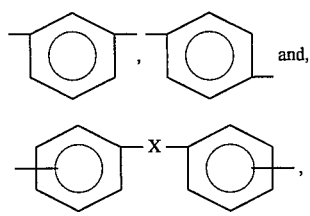

wherein the catenation is selected from the group consisting of 2,2'; 2,3'; 2,4'; 3,3'; 3,4'; and 4,4' and X is a bond or X is a radical selected from the group consisting of:

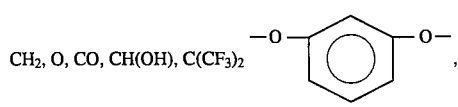

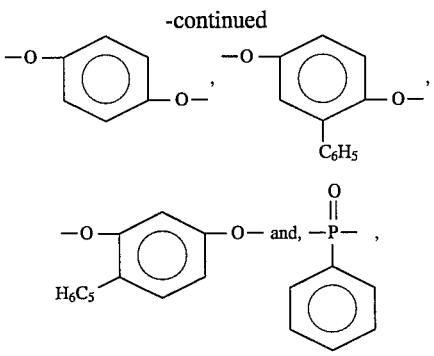

wherein Z is a radical selected from the group consisting of: H,

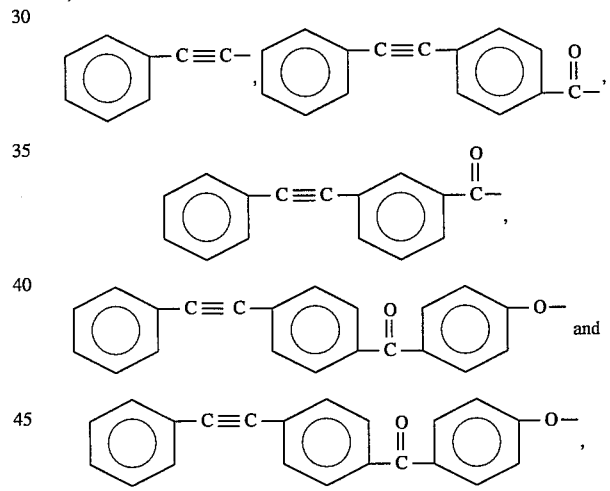

wherein R is a radical selected from the group consisting of:

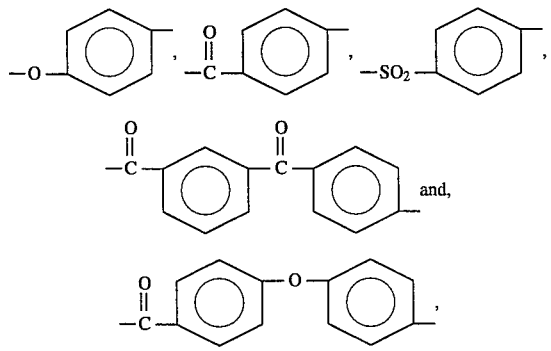

wherein the amount of diamine containing pendent phenylethynyl groups ranges from 1–99 mole %.

17. Controlled molecular weight amic acid co-oligomers containing pendent phenylethynyl groups of claim 16 wherein Ar is a radical represented by:

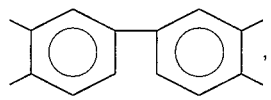

wherein Ar' is a radical represented by:

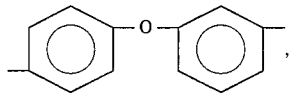

wherein W is is a radical represented by:

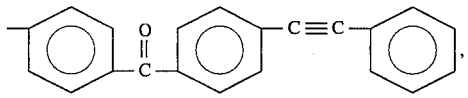

wherein the amount of diamine containing pendent phenylethynyl is 15 mole %.

18. Controlled molecular weight amic acid co-oligomers containing pendent phenylethynyl groups of claim 16 wherein Ar' is a radical represented by:

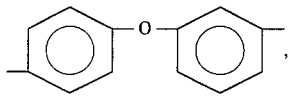

wherein Ar is a radical represented by

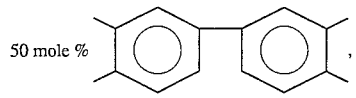

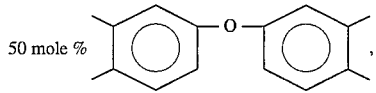

Z is a radical represented by:

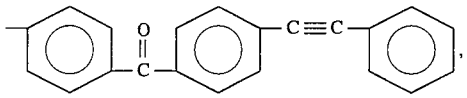

wherein the amount of diamine containing pendent phenylethynyl groups is 10 or 15 mole %.

19. Controlled molecular weight amic acid oligomers containing pendent phenylethynyl groups and chain terminated with either nonreactive or reactive phthalic anhydride based endcapping agents have the following repeat unit:

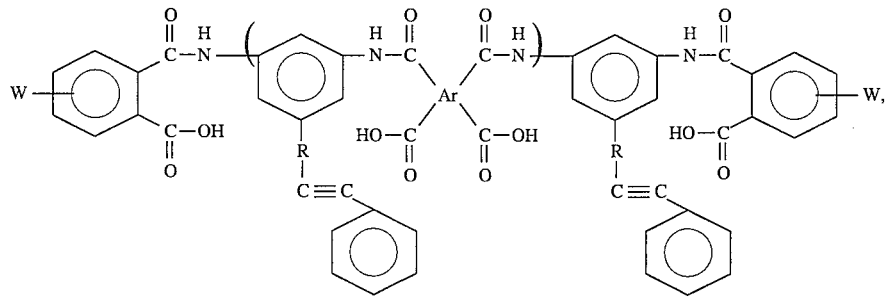

wherein Ar is a member selected from the group consisting of:

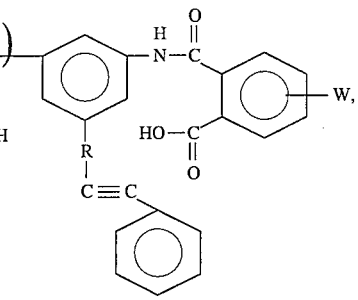

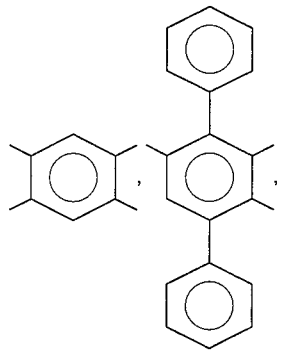

wherein Y is a bond or Y is a radical selected from the group consisting of:
  O, CO, SO$_2$, C(CF$_3$)$_2$, isophthalpyl, terephthaloyl, 1,3-diphenoxy and 1,4-diphenoxy,
wherein W is a radical selected from the group consisting of: H,

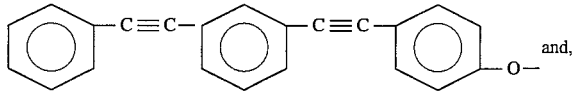

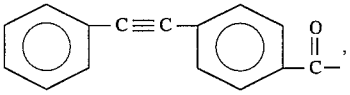

wherein R is a radical selected from the group consisting of:

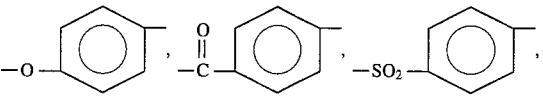

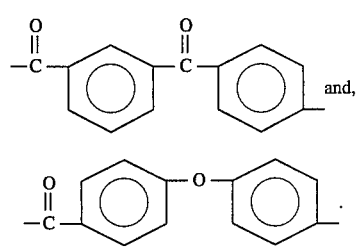
and,

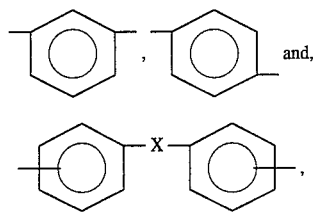
and, wherein Z is a radical selected from the group consisting of: H, 20. Controlled molecular weight amic acid oligomers containing pendent phenylethynyl groups and chain terminated with either nonreactive or reactive aniline based endcapping agents have the following repeat unit:

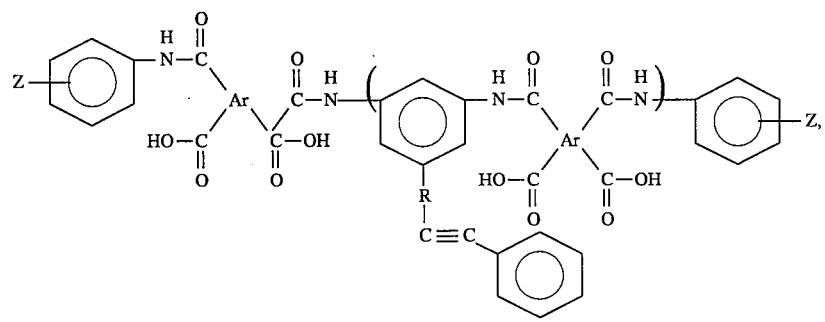

wherein Ar is a member selected from the group consisting of:

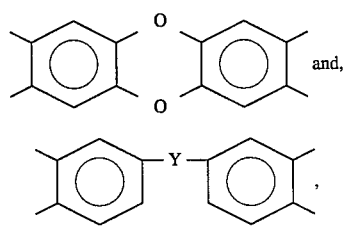

wherein Y is a bond or Y is a radical selected from the group consisting of:

O, CO, $SO_2$, $C(CF_3)_2$, isophthaloyl, terephthaloyl, 1,3-diphenoxy and 1,4-diphenoxy, wherein Ar' is a member selected from the group consisting of:

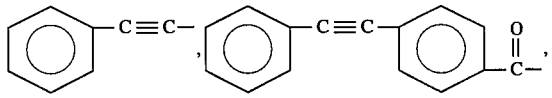

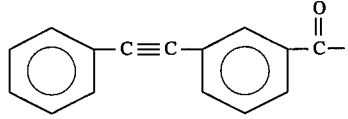

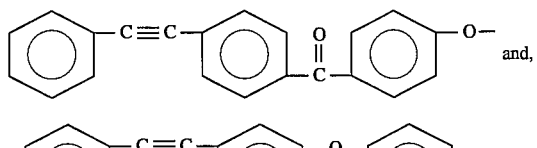

and,

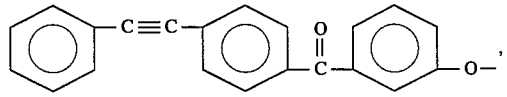

wherein R is a radical selected from the group consisting of:

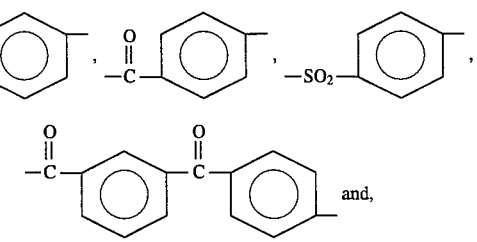

and,

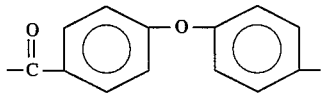

21. A process for synthesizing controlled molecular weight copolyimides containing pendent phenylethynyl groups and chain terminated with either nonreactive or reactive phthalic anhydride based endcapping agents of claim 1 in which:

the process comprises cyclodehydrating precursor amic acid co-oligomers containing pendent phenylethynyl groups having the general structural formula:

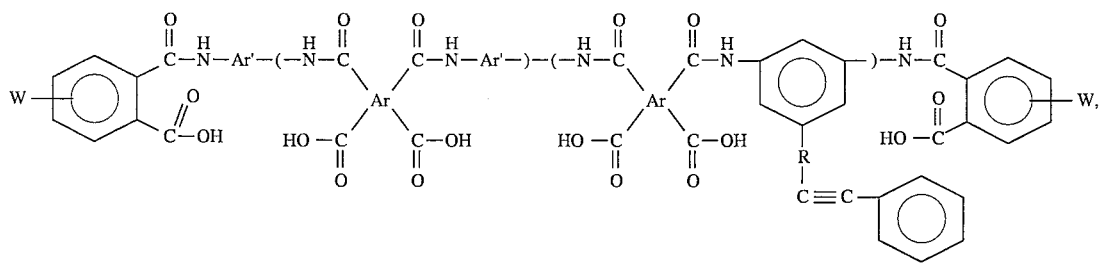

wherein the cyclodehydrating reaction is carried out in a polar solvent such as N,N-dimethylacetamide, N-methyl-2-pyrrolidinone, N-cyclohexyl-2-pyrrolidinone, m-cresol, dimethylsulfoxide, sulfolane, or γ-butrolactone; wherein the cyclodehydrating reaction is carried out with the application of heat and in the presence of a dehydrating agent such as toluene, xylenes, acetic acid, acetic anhydride, isoquinoline or chlorobenzene.

22. A process for synthesizing controlled molecular weight copolyimides containing pendent phenylethynyl groups and chain terminated with either nonreactive or reactive phthalic anhydride based endcapping agents of claim 5 in which:

the process comprises cyclodehydrating precursor amic acid co-oligomers containing pendent phenylethynyl groups having the general structural formula:

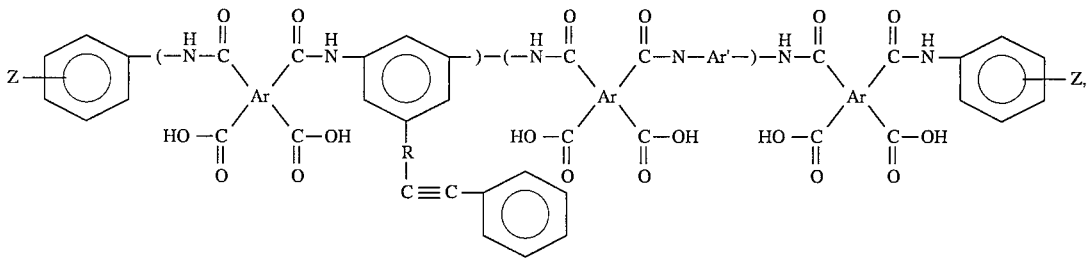

wherein the cyclodehydrating reaction is carried out in a polar solvent such as N,N-dimethylacetamide, N-methyl-2-pyrrolidinone, N-cyclohexyl-2-pyrrolidinone, m-cresol, dimethylsulfoxide, sulfolane, or γ-butrolactone; wherein the cyclodehydrating reaction is carried out with the application of heat and in the presence of a dehydrating agent such as toluene, xylenes, acetic acid, acetic anhydride, isoquinoline or chlorobenzene.

23. A cured film prepared from a controlled molecular weight imide co-oligomer containing pendent phenylethynyl groups of claim 1.

24. A cured film prepared from a controlled molecular weight imide co-oligomer containing pendent phenylethynyl groups of claim 5.

25. A cured film prepared from a controlled molecular weight imide oligomer containing pendent phenylethynyl groups of claim 8.

26. A cured film prepared from a controlled molecular weight imide oligomer containing pendent phenylethynyl groups of claim 9.

27. A cured film prepared from a imide oligomer containing pendent phenylethynyl groups of claim 11.

28. A cured film cast from a solution of an amic acid co-oligomer containing pendent phenylethynyl groups of claim 11 wherein the solution comprises a polar solvent selected from the group consisting of: as N,N-dimethylacetamide, N-methyl-2-pyrrolidinone, N-cyclohexyl-2-pyrrolidinone, m-cresol, dimethylsulfoxide, sulfolane, or γ-butrolactone; and wherein the reaction is carried out with the application of heat; and wherein the reaction is carried out in the presence of dehydrating agents selected from the group consisting of: toluene, xylenes, isoquinoline, chlorobenzene or acetic anhydride.

29. A cured film cast from a solution of an amic acid co-oligomer containing pendent phenylethynyl groups of claim 11, wherein the solution comprises a polar solvent selected from the group consisting of: N,N-dimethylacetamide, N-methyl-2-pyrrolidinone, N-cyclohexyl-2-pyrrolidinone, m-cresol, dimethylsulfoxide, sulfolane, or γ-butrolactone.

30. A cured film cast from a solution of an amic acid co-oligomer containing pendent phenylethynyl groups of claim 15, wherein the solution comprises a polar solvent selected from the group consisting of: N,N-dimethylacetamide, N-methyl-2-pyrrolidinone, N-cyclohexyl-2-pyrrolidinone, m-cresol, dimethylsulfoxide, sulfolane, or γ-butrolactone.

31. A cured film according to claim 23 which is prepared by molding imide powder by the application of heat and pressure.

32. A cured film according to claim 24 which is prepared by molding imide powder by the application of heat and pressure.

33. An uncured film according to claim 25 where the cyclodehydration and solvent removal is carried out by the application of heat such that the reaction of the phenylethynyl groups does not occur.

34. An uncured film according to claim 29 where the cyclodehydration and solvent removal is carried out by the application of heat such that the reaction of the phenylethynyl groups does not occur.

35. A neat resin molding prepared from a controlled molecular weight imide co-oligomer containing pendent phenylethynyl groups of claim 1.

36. A neat resin molding prepared from a controlled molecular weight imide co-oligomer containing pendent phenylethynyl groups of claim 5.

37. A cured neat resin molding according to claim 35 which is prepared by the application of heat and pressure.

38. A cured neat resin molding according to claim 36 which is prepared by the application of heat and pressure.

39. A cured adhesive prepared from a controlled molecular weight imide co-oligomer containing pendent phenylethynyl groups according to claim 1.

40. A cured adhesive prepared from a controlled molecular weight imide co-oligomer containing pendent phenylethynyl groups according to claim 5.

41. A cured adhesive according to claim 39, which is prepared by the application of heat and pressure.

42. A cured adhesive according to claim 40, which is prepared by the application of heat and pressure.

43. A composite prepared from a controlled molecular weight imide co-oligomer containing pendent phenylethynyl groups according to claim 1.

44. A composite prepared from a controlled molecular weight imide co-oligomer containing pendent phenylethynyl groups according to claim 5.

* * * * *